US010653327B2

(12) United States Patent
Iijima

(10) Patent No.: US 10,653,327 B2
(45) Date of Patent: May 19, 2020

(54) BIOLOGICAL INFORMATION DETECTION DEVICE

(71) Applicant: Seiko Epson Corporation, Tokyo (JP)

(72) Inventor: Yoshitaka Iijima, Oomachi (JP)

(73) Assignee: Seiko Epson Corporation, Tokyo (JP)

( * ) Notice: Subject to any disclaimer, the term of this patent is extended or adjusted under 35 U.S.C. 154(b) by 995 days.

(21) Appl. No.: 14/833,267

(22) Filed: Aug. 24, 2015

(65) Prior Publication Data

US 2016/0058310 A1 Mar. 3, 2016

(30) Foreign Application Priority Data

Aug. 27, 2014 (JP) ................. 2014-172814

(51) Int. Cl.
*A61B 5/1455* (2006.01)
*A61B 5/024* (2006.01)
*A61B 5/00* (2006.01)

(52) U.S. Cl.
CPC ...... *A61B 5/02427* (2013.01); *A61B 5/02438* (2013.01); *A61B 5/681* (2013.01); *A61B 5/6843* (2013.01); *A61B 5/7214* (2013.01); *A61B 2562/0233* (2013.01); *A61B 2562/185* (2013.01)

(58) Field of Classification Search
None
See application file for complete search history.

(56) References Cited

U.S. PATENT DOCUMENTS

| 7,123,351 B1* | 10/2006 | Schaefer | G01C 3/08 356/4.07 |
| 8,723,790 B1* | 5/2014 | Schaefer | G06F 3/011 345/156 |
| 8,740,791 B2 | 6/2014 | Sato et al. | |
| 2004/0193063 A1 | 9/2004 | Kimura et al. | |
| 2007/0164240 A1* | 7/2007 | Shinno | G01B 11/303 250/559.4 |
| 2011/0133941 A1* | 6/2011 | Yao | G01J 1/02 340/600 |
| 2012/0078116 A1 | 3/2012 | Yamashita | |
| 2012/0160994 A1* | 6/2012 | Costello | G01D 11/245 250/221 |
| 2013/0204143 A1 | 8/2013 | Narusawa | |
| 2014/0016132 A1* | 1/2014 | Schmitz | A61B 5/14551 356/343 |
| 2014/0275852 A1* | 9/2014 | Hong | A61B 5/02427 600/301 |
| 2014/0276149 A1* | 9/2014 | Takahashi | A61B 5/02438 600/503 |

FOREIGN PATENT DOCUMENTS

| EP | 0756849 A1 * | 2/1997 | ......... A61B 5/02416 |
| JP | 2004-261366 A | 9/2004 | |
| JP | 2011-139725 A | 7/2011 | |
| JP | 2012-070828 A | 4/2012 | |
| JP | 2013-176535 A | 9/2013 | |

* cited by examiner

*Primary Examiner* — Patricia J Park
(74) *Attorney, Agent, or Firm* — ALG Intellectual Property, LLC

(57) ABSTRACT

A biological information detection device includes: a light emitting unit which irradiates a subject with light; a first light receiving unit which receives light from the subject; a second light receiving unit which receives light from the subject; and a beam which is provided between the first light receiving unit and the second light receiving unit, in a plan view in a vertical direction of a light receiving surface of the first light receiving unit.

20 Claims, 17 Drawing Sheets

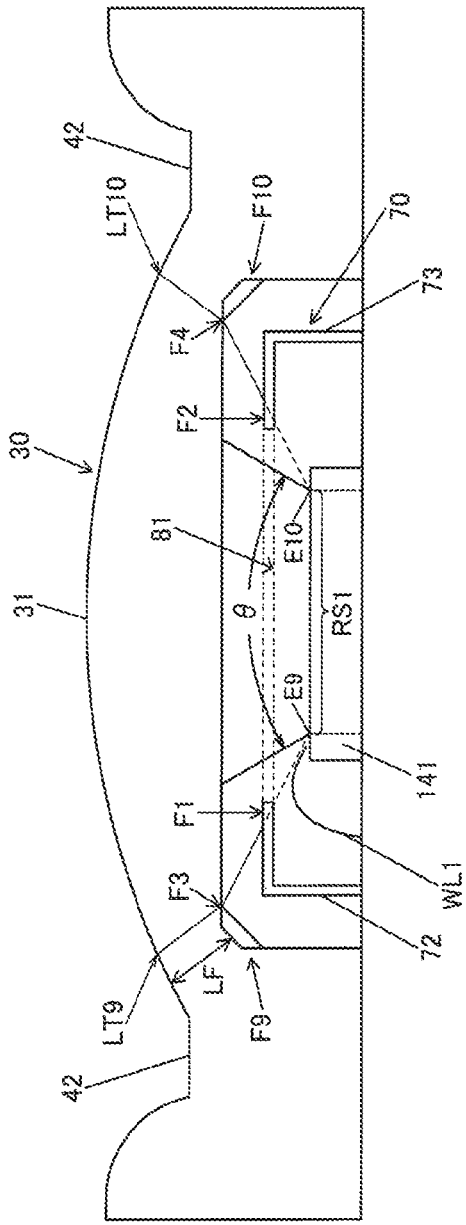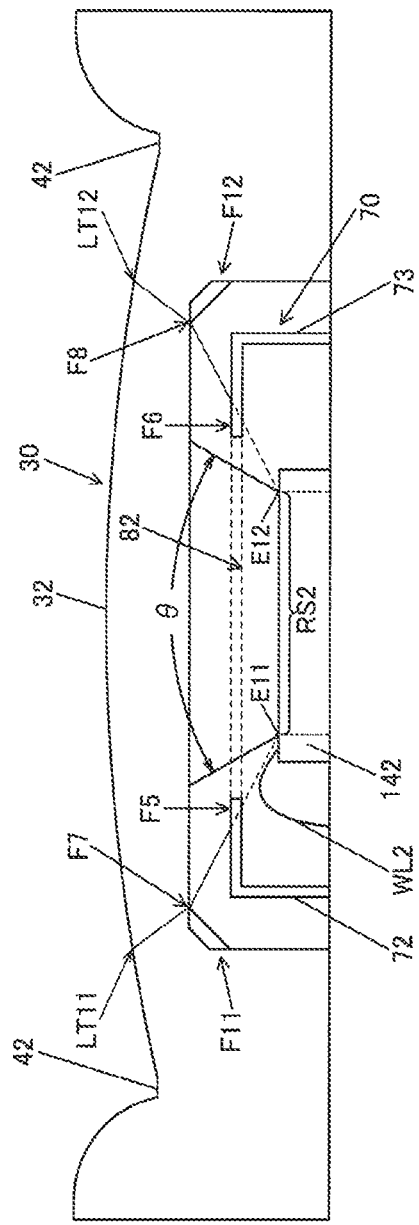
FIG. 5A
FIG. 5B

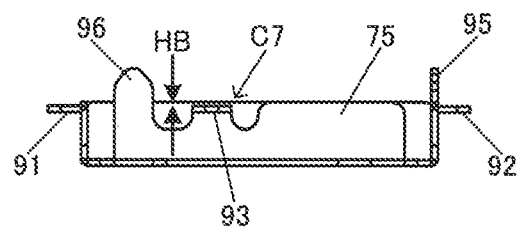
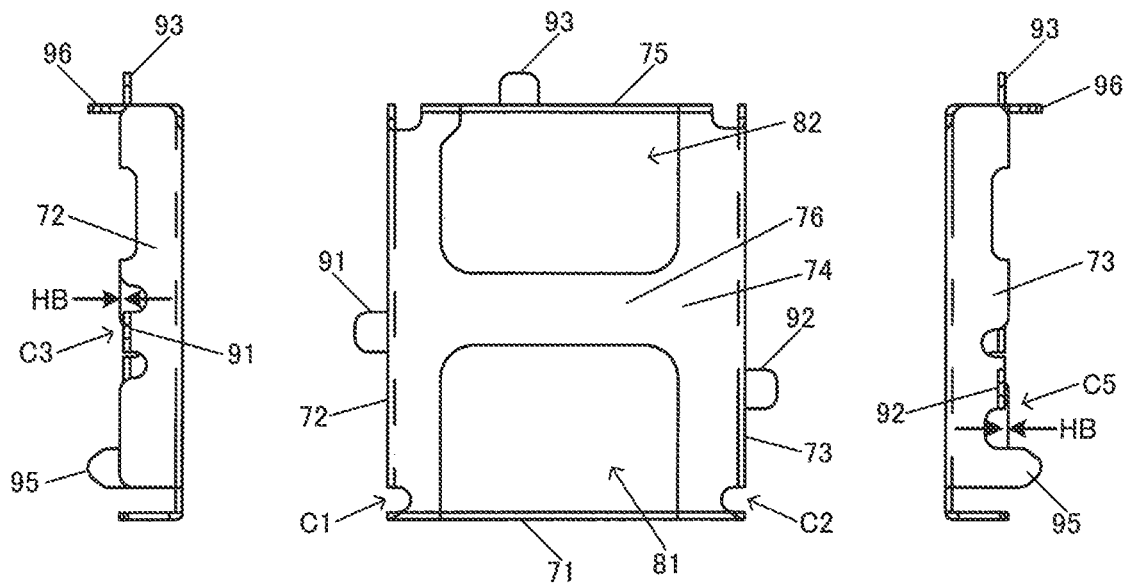
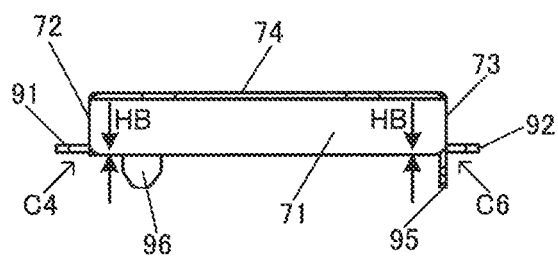
FIG. 8

BIOLOGICAL INFORMATION DETECTION DEVICE

This application claims priority to Japanese Patent Application No. 2014-172814, filed Aug. 27, 2014, the entirety of which is hereby incorporated by reference.

BACKGROUND

1. Technical Field

The present invention relates to a biological information detection device.

2. Related Art

In the related art, a biological information detection device which detects biological information such as the pulse wave of a human being has been known. JP-A-2011-139725 and JP-A-2013-176535 disclose techniques of the related art regarding a pulse wave detection device which is an example of such a biological information detection device.

The device disclosed in JP-A-2011-139725 and JP-A-2013-176535 is a photoelectric pulse wave detection device in which a light emitting unit which emits light towards a subject which is a target and a light receiving unit which receives light (light including biological information) from the subject are provided in a sensor unit. A pulse wave is detected by detecting a change in a blood flow as a change in a light receiving amount using the sensor unit.

JP-A-2013-176535 discloses a sensor unit having a configuration in which a plurality of light receiving units (photodiodes) are disposed for one light emitting unit (LED). However, when embedding the sensor unit into an actual device, it is necessary to regulate light causing noise and to appropriately irradiate the light receiving unit with light which is a detection target of each light receiving unit, in order to ensure reliability of a detection signal of each light receiving unit of the plurality of light receiving units. The regulation of light causing noise can be realized by providing a light shielding structure in the sensor unit, for example, but a light shielding structure satisfying the above requirements is not provided in the configuration in that the plurality of light receiving units are disposed.

SUMMARY

An advantage of some aspects of the invention is to provide a biological information detection device which can realize an appropriate light shielding structure in a configuration in that a plurality of light receiving units are provided.

An aspect of the invention relates to a biological information detection device including: a light emitting unit which irradiates a subject with light; a first light receiving unit which receives light from the subject; a second light receiving unit which receives light from the subject; and a beam which is provided between the first light receiving unit and the second light receiving unit, in a plan view in a vertical direction of a light receiving surface of the first light receiving unit.

According to the aspect of the invention, the light emitting unit irradiates the subject with light and the first and second light receiving units receive light from the subject or the like. In a plan view in a vertical direction of the light receiving surface of the first light receiving unit, the beam is provided between the first light receiving unit and the second light receiving unit. By providing the beam, it is possible to regulate light receiving of unnecessary incident light or to ensure strength, and it is possible to realize a proper light shielding structure in the configuration of providing the plurality of light receiving units.

In the aspect of the invention, the first light receiving unit and the second light receiving unit may be disposed along a first direction, and when a distance in the first direction between an end portion of the beam on the first light receiving unit side and an end portion of the first light receiving unit on the second light receiving unit side is set as LE1, and a distance in the first direction between an end portion of the beam on the second light receiving unit side and an end portion of the second light receiving unit on the first light receiving unit side is set as LE2, a relationship of LE1>LE2 may be satisfied.

With this configuration, the beam is provided in a position shifted to the second light receiving unit side, for example, and it is possible to property regulate incident light to the first and second light receiving units or to ensure strength of the beam.

In the aspect of the invention, the biological information detection device may further include a light transmitting member which is provided on a position on the subject side with respect to the first light receiving unit and the second light receiving unit, passes light from the subject, and comes into contact with the subject when measuring biological information of the subject to apply a pressing force.

With this configuration, it is possible to emit light from the subject to the first and second light receiving units through the light transmitting member while applying a pressing force to the subject by the light transmitting member.

In the aspect of the invention, the light transmitting member may include a first protrusion corresponding to the first light receiving unit and a second protrusion corresponding to the second light receiving unit, and the beam may shield light so that light which has passed a boundary between the first protrusion and the second protrusion is not incident to the light receiving surface of the first light receiving unit.

With this configuration, the light which has passed the boundary between the first protrusion and the second protrusion is emitted to the first light receiving unit, and accordingly, it is possible to prevent a phenomenon of affecting negative effects on the detection results of the first light receiving unit.

In the aspect of the invention, the light transmitting member may include a first protrusion corresponding to the first light receiving unit and a second protrusion corresponding to the second light receiving unit, and the beam may be positioned on a position so as not to shield light which passes a position on the second protrusion side than a total reflection boundary of the first protrusion and is incident to a point where a distance to the beam is shortest among the light receiving surface of the second light receiving unit.

With this configuration, light transmitted through the position on the second protrusion side other than the total reflection boundary of the first protrusion is emitted to the second light receiving unit, and accordingly, it is possible to increase the width of the beam while ensuring the light receiving amount of the second light receiving unit and to ensure the strength of the beam.

In the aspect of the invention, the light transmitting member may include a first protrusion corresponding to the first light receiving unit and a second protrusion corresponding to the second light receiving unit, and the biological information detection device may further include a pressing force prevention unit which is provided so as to cover the first and second protrusions and prevents a pressing force applied to the subject by the first protrusion.

With this configuration, it is possible to prevent the pressing force applied to the subject by the first protrusion by pressing force prevention unit to reduce fluctuation in a pressing force. When an amount of change of the pressing force of the first protrusion with respect to the load by the load mechanism for generating the pressing force of the first protrusion is set as a pressing force change amount, the pressing force prevention unit may prevent the pressing force applied to the subject by the first protrusion so that the pressing force change amount in a second load range where a load of the load mechanism is larger than FL1 becomes small, compared to a pressing force change amount in a first load range where a load of the load mechanism is 0 to FL1.

In the aspect of the invention, when a height of the light transmitting member in a position or an area corresponding to the first light receiving unit in a direction from a biological information detection device to the subject is set as h1 and a height of the light transmitting member in a position or an area corresponding to the second light receiving unit is set as h2, a relationship of h1>h2 may be satisfied.

With this configuration, the heights of the light transmitting member in a position or an area corresponding to the first light receiving unit and the second light receiving unit are different from each other. Accordingly, since the difference in the pressing force can be set, for example, it is possible to differentiate the characteristics between the first detection signal from the first light receiving unit and the second detection signal from the second light receiving unit. It is possible to detect biological information based on the first and second detection signals having different characteristics.

In the aspect of the invention, the first light receiving unit may be disposed between the light emitting unit and the second light receiving unit.

With this configuration, the first light receiving unit is disposed to be close to the light emitting unit, and accordingly, it is possible to operate biological information based on the first detection signal of the first light receiving unit. When a distance between the light emitting unit and the first light receiving unit is set as L1 and a distance between the light emitting unit and the second light receiving unit is set as L2, a relationship of L2>2×L1 may be satisfied.

In the aspect of the invention, the biological information detection device may further include a processing unit which operates the biological information of the subject based on a first detection signal detected by the first light receiving unit.

With this configuration, it is possible to operate biological information based on the first detection signal.

In the aspect of the invention, the processing unit may perform a noise reduction process of the first detection signal based on a second detection signal detected by the second light receiving unit.

With this configuration, it is possible to realize the operation process of biological information by performing the noise reduction process of the first detection signal based on the second detection signal of the second light receiving unit.

In the aspect of the invention, the biological information detection device may further include a light shielding member which is provided so as to surround at least the first light receiving unit and the second light receiving unit, and includes a first opening corresponding to the first light receiving unit and a second opening corresponding to the second light receiving unit, in which the beam is provided between the first opening and the second opening.

With this configuration, it is possible to realize apertures of the first and second light receiving units, for example, by providing the light shielding member including the first and second openings corresponding to the first and second light receiving units. In addition, by providing the beam between the first opening and the second opening, it is possible to improve detection performance of a biological information detection device and to ensure the strength of the light shielding member, for example, and it is possible to realize a proper light shielding structure in the configuration of providing the plurality of light receiving units.

In the aspect of the invention, the biological information detection device may further include a light shielding member which includes first to third light shielding surfaces and the beam, in which the first light shielding surface is provided between the light emitting unit and the first light receiving unit, and the second light shielding surface and the third light shielding surface are provided so as to intersect the first light shielding surface.

For example, by providing the first light shielding surface between the light emitting unit and the first light receiving unit, it is possible to prevent emission of the direct light from the light emitting unit to the first light receiving unit and the detection performance of the biological information detection device is improved. By providing the second and third light shielding surfaces, it is also possible to shield the light on the side surface side, for example.

In the aspect of the invention, the light shielding member may be formed by sheet metal working of metal.

With this configuration, when the light shielding member is formed by sheet metal working of metal, it is possible to decrease the thickness of the metal surface while ensuring the strength of the light shielding member.

In the aspect of the invention, the first light shielding surface and the second light shielding surface may be provided so as to be adjacent to each other through a first gap area, and the first light shielding surface and the third light shielding surface may be provided so as to be adjacent to each other through a second gap area.

With this configuration, when the first and second gap areas are provided, it is possible to prevent a phenomenon in that distortion occurs in a folded part at the time of the sheet metal working of the light shielding member and folding processing is not excellently performed.

In the aspect of the invention, a first opening corresponding to the first light receiving unit may be provided by the first light shielding surface, the second light shielding surface, the third light shielding surface, and the beam.

With this configuration, it is possible to provide the first opening functioning as an aperture of the first light receiving unit by the first, second, and third light shielding surfaces and the beam.

In the aspect of the invention, a first opening corresponding to the first light receiving unit may be provided by the first light shielding surface, the beam, and eaves.

With this configuration, it is possible to provide the first opening functioning as an aperture of the first light receiving unit by the first light shielding surface, the beam, and eaves.

In the aspect of the invention, the light shielding member may include a protrusion, and the protrusion may be provided so that an attachment surface of the protrusion is positioned at a distance of a height HB (HB>0) from an installation surface of the substrate to which the light shielding member is mounted.

With this configuration, a space between the attachment surface of the protrusion and an installation surface of the substrate is effectively used, and accordingly, it is possible to realize proper attachment of the light shielding member to the substrate.

BRIEF DESCRIPTION OF THE DRAWINGS

The invention will be described with reference to the accompanying drawings, wherein like numbers reference like elements.

FIGS. 5A and 5B are also sectional views of the sensor unit of the biological information detection device.

FIG. 8 is a plan view, a side view, a front view, and a rear view showing a specific example of the light shielding member.

DESCRIPTION OF EXEMPLARY EMBODIMENTS

Hereinafter, the embodiments will be described. The embodiments which will be described hereinafter do not unjustly limit the content of the invention disclosed in the aspect. In addition, all configurations illustrated in the embodiments are not necessarily compulsory configuration requirements of the invention.

1. Entire Configuration of Biological Information Detection Device

Figure 1:
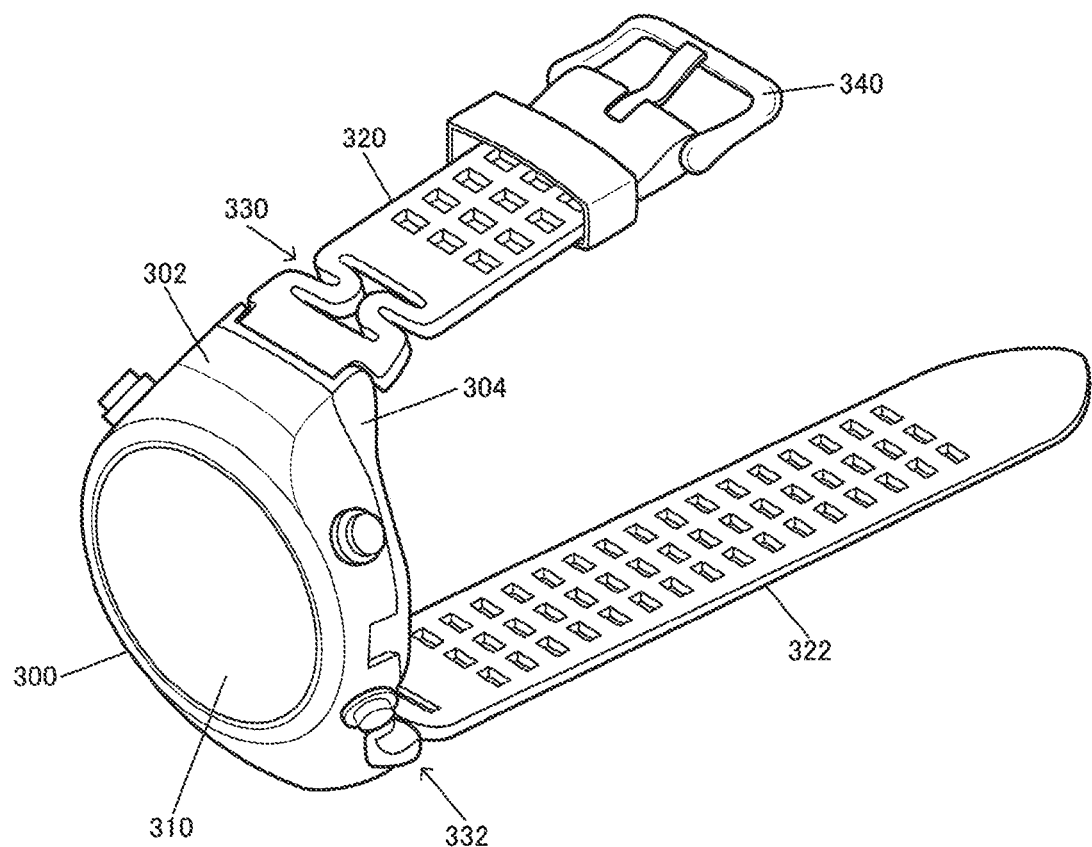
FIG. 1 is an example of a biological information detection device of the embodiment.
Figure 2:
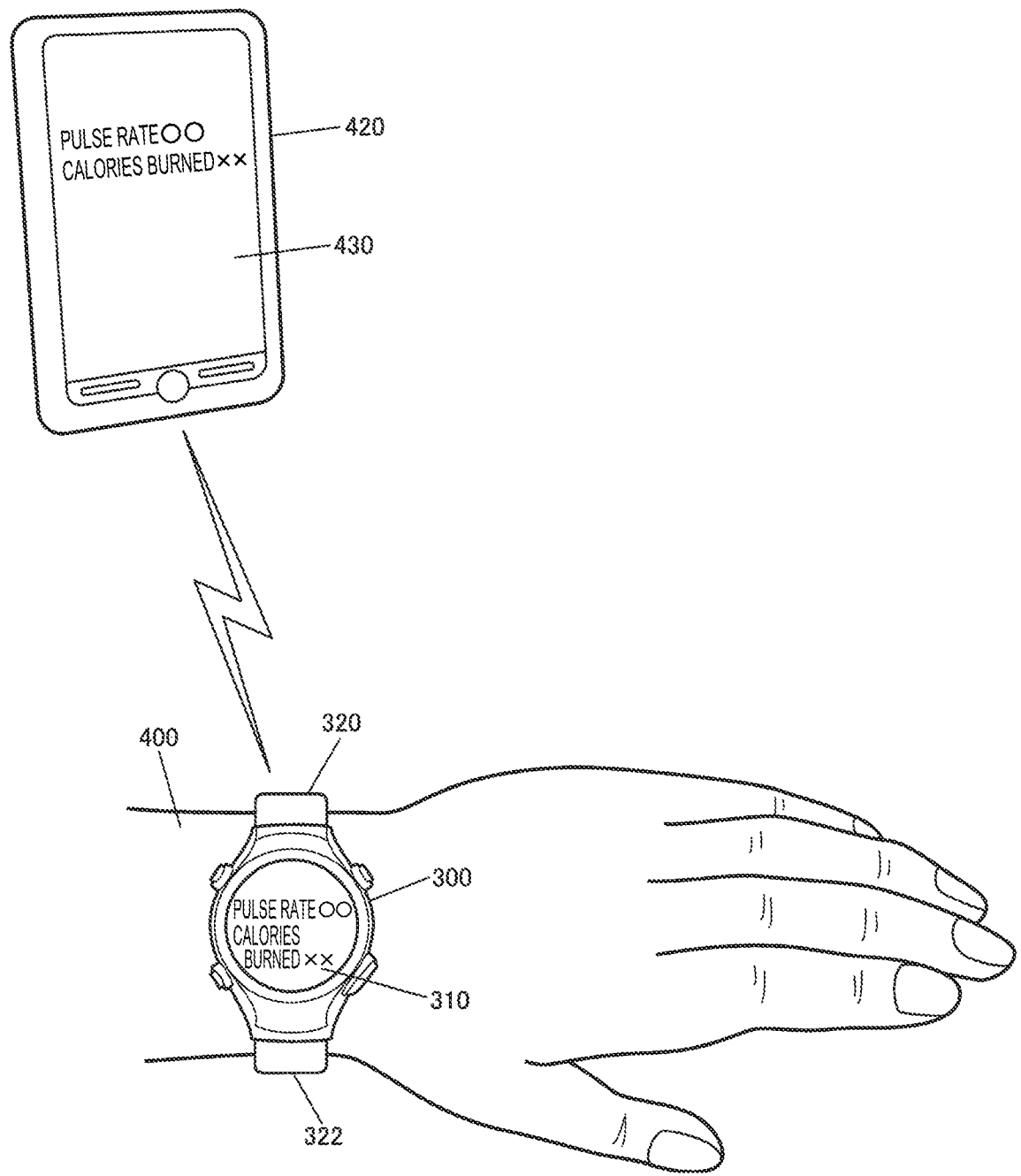
FIG. 2 is an explanatory diagram regarding the wearing of the biological information detection device and communication with a terminal device.

First, an example of the entire configuration of a biological information detection device of the embodiment will be described. FIG. 1 is a perspective view of an example of the biological information detection device of the embodiment. The biological information detection device (biological information measurement device) is a watch type device, and is worn on a wrist 400 (a given part in a broad sense) of a user, as shown in FIG. 2, and detects biological information such as pulse wave information and the like. The biological information detection device includes a case 300 (main body unit) and bands 320 and 322 for mounting the case 300 on a user. Hereinafter, a case where the biological information detection device is a watch type pulsimeter to be worn on the wrist will be described as an example, but the embodiment is not limited thereto. The biological information detection device of the embodiment may be worn on a part other than the wrist (for example, finger, upper arm, or breast) and detect (measure) biological information, for example. The biological information which is a detection target of the biological information detection device is not limited to a pulse wave (pulse rate) either, and the biological information detection device may be a device which detects biological information other than a pulse wave (for example, oxygen saturation in blood, body temperature, heart rate, or blood pressure).

The case 300 accommodates each unit of the biological information detection device such as a sensor unit 130 and a processing unit 200 of FIG. 10 will be described later. The case 300 is a main body unit which is attached to a user and detects biological information. In FIG. 1, the case 300 (main body unit) is configured with a top case 302 and a bottom case 304 (back cover unit). A display unit 310 such as an LCD is provided on the top case 302. As shown in FIG. 2, various information items such as pulse rate (biological detection information in the broad sense), calories burned (active state information in the broad sense), or time are displayed on the display unit 310. The case 300 may not have a structure separated into the top case 302 and the bottom case 304 as described above.

The biological information detection device is connected to and communicates with a terminal device 420 so as to transmit and receive data. The terminal device 420 is a portable communication terminal such as a smart phone, a mobile phone, or a feature phone, for example. Alternatively, the terminal device 420 may be an information processing terminal such as a tablet type computer. As the communication connection between the biological information detection device and the terminal device 420, near field communication such as Bluetooth (registered trademark) can be used, for example. The biological information detection device and the terminal device 420 are connected and communicate with each other as described above, and accordingly various information items such as a heart rate or calories burned can be displayed on the display unit 430 (LCD or the like) of the terminal device 420. An operation process of the information, such as heart rate or calories burned, may be executed in the biological information detection device or at least a part thereof may be executed in the terminal device 420.

The bands 320 and 322 include expansion and contraction portions 330 and 332 or a buckle 340. The bands 320 and 322 come into contact with the case 300 which is the main body unit through the expansion and contraction portions 330 and 332. The expansion and contraction portions 330 and 332 expand and contract along a direction orthogonal to a longitudinal direction of the wrist of a user. The biological information detection device is worn on the wrist 400 of a user by fitting one end of the band 322 to the buckle 340. A load mechanism of the embodiment is realized with the expansion and contraction portions 330 and 332 and the bands 320 and 322 which are elastic members. Since a tensile force of the expansion and contraction portions 330 and 332 and the bands 320 and 322 is operated, it is possible to ensure an assumed appropriate pressing force of first and second protrusions 31 and 32 of a light transmitting member 30, which will be described later in FIGS. 3A to 5B, that is applied to a subject, to some extent.

2. Sensor Unit

Figure 3A:
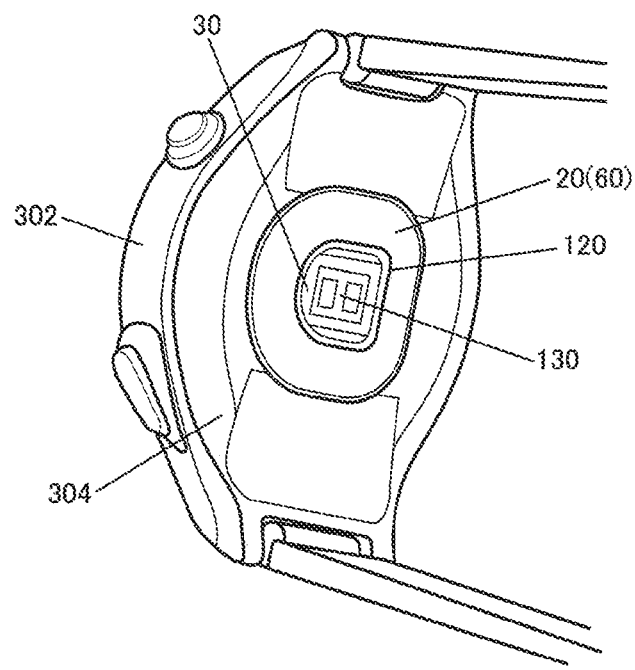
FIGS. 3A and 3B are explanatory diagrams of a sensor unit of the biological information detection device.

Next, the sensor unit 130 of the biological information detection device of the embodiment will be described in detail. FIG. 3A is a perspective view when the biological information detection device is seen from the bottom case 304 side (subject side). As shown in FIG. 3A, a detection window 120 for detecting biological information such as a pulse wave is provided on the bottom case 304 (case in the broad sense) and the sensor unit 130 is provided in a position corresponding to the detection window 120.

Figure 3B:
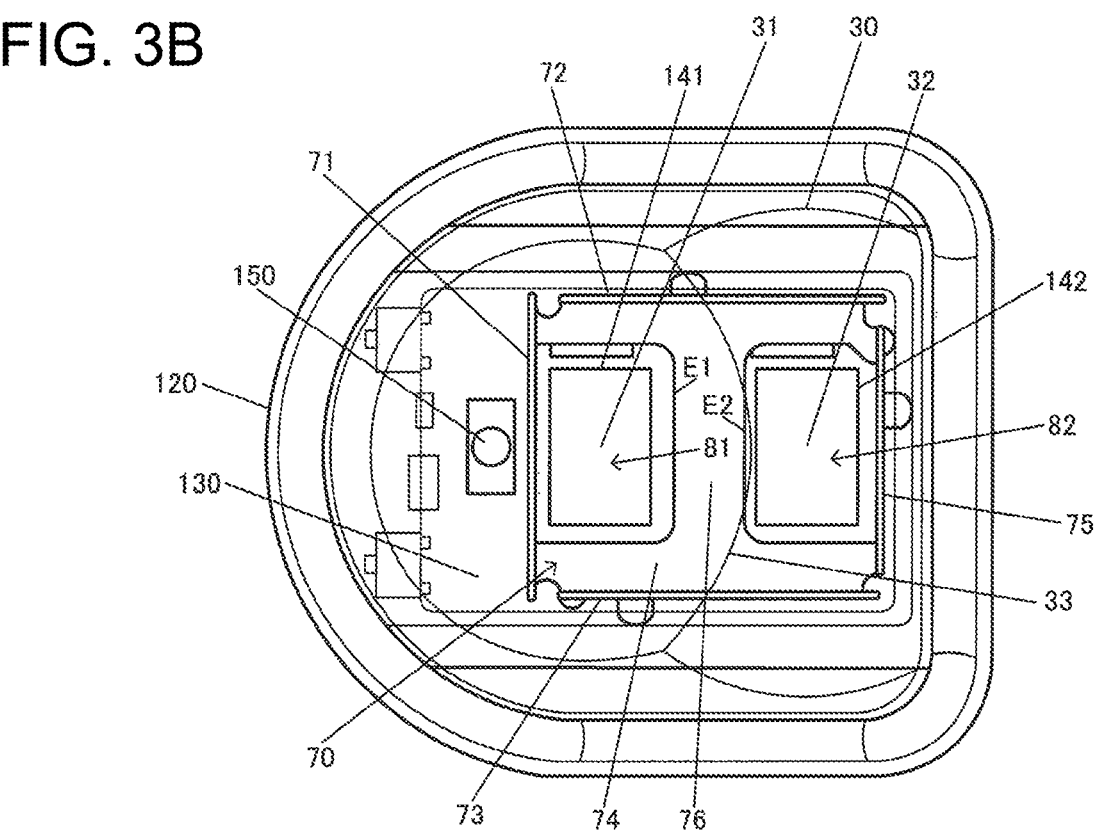
Figure 4:
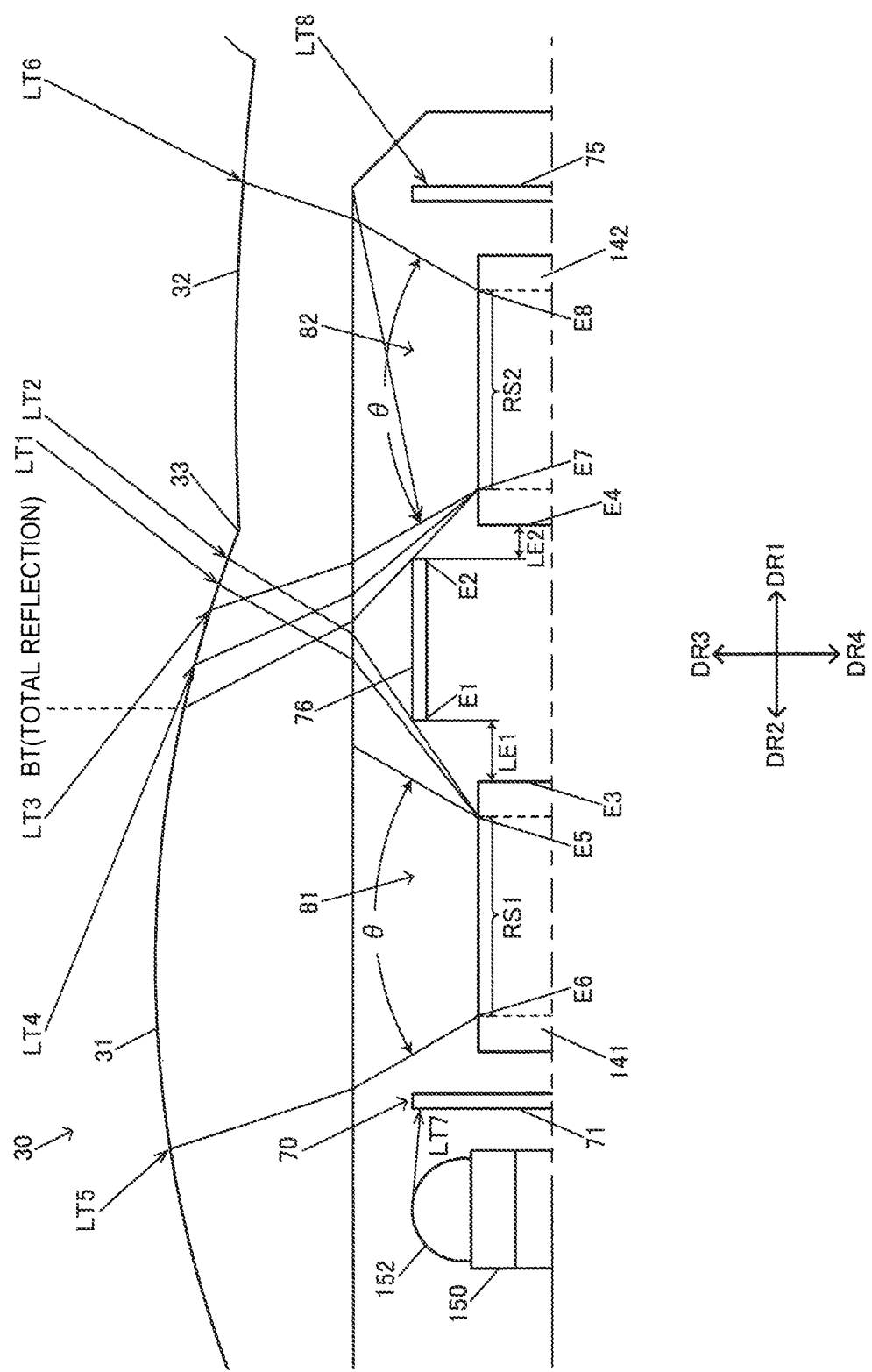
FIG. 4 is a sectional view of the sensor unit of the biological information detection device.

FIG. 3B is a plan view when the sensor unit 130 is seen from the bottom case 304 side (subject side) and FIGS. 4, 5A, and 5B are sectional views of the sensor unit 130. Specifically, FIG. 4 is a sectional view of a surface crossing a light emitting unit 150 and first and second light receiving units 141 and 142 which configure the sensor unit 130. FIG. 5A is a sectional view of a surface crossing the first light receiving unit 141 and FIG. 5B is a sectional view of a surface crossing the second light receiving unit 142.

As shown in FIGS. 3A to 5B, the biological information detection device of the embodiment includes the light emitting unit 150 which emits light to a subject (a user or the wrist of a user) and the first and second light receiving units 141 and 142 which receive light from a subject. In a plan view in a vertical direction (DR4 direction) of a light receiving surface RS1 of the first light receiving unit 141, a beam 76 is provided between the first light receiving unit 141 and the second light receiving unit 142. Specifically, the biological information detection device of the embodiment can include a light shielding member 70. The light shielding member 70 is, for example, provided so as to surround at least the first light receiving unit 141 and the second light receiving unit 142, for example. The light shielding member 70 includes a first opening 81 (first aperture) corresponding to the first light receiving unit 141 and a second opening 82 (second aperture) corresponding to the second light receiving unit 142. The beam 76 is provided between the first opening 81 and the second opening 82. Specifically, the beam 76 is provided between the first opening 81 and the second opening 82, in a plan view in the vertical direction (DR4 direction) of the light receiving surface RS1 of the first light receiving unit 141. Hereinafter, a case including the two light receiving units will be described, but the number of light receiving units may be three or more. Hereinafter, a case where the beam 76 is provided as a part of the light shielding member 70 will be described as an example, but the beam 76 may be provided as a separate member from the light shielding member 70.

The biological information detection device of the embodiment can include a light transmitting member 30. The light transmitting member 30 is provided at a position on a subject side with respect to the positions of the first light receiving unit 141 and the second light receiving unit 142. The light transmitting member is, for example, provided on a housing surface side (housing surface of the bottom case) which comes into contact with a subject of the biological information detection device. The light transmitting member 30 transmits light from a subject and comes in contact with a subject when measuring biological information of a subject to apply a pressing force. The light transmitting member 30, for example, transmits light incident to the first and second light receiving units 141 and 142 (light from a subject). In addition, the light transmitting member 30 transmits light emitted from the light emitting unit 150. The light transmitting member 30 includes a first protrusion 31 corresponding to the first light receiving unit 141 and a second protrusion 32 corresponding to the second light receiving unit 142. That is, the light transmitting member includes the first and second protrusions 31 and 32 which come into contact with a subject and apply a pressing force when measuring biological information of a subject. A surface shape of the first and second protrusions 31 and 32 is desired to be a curved surface shape (spherical surface shape), but there is no limitation and various shapes can be exemplified. Any material may be used as long as the light transmitting member 30 is transparent with respect to a wavelength of light from a subject, and a transparent material may be used or a colored material may be used.

As shown in FIG. 3A, apart of the light transmitting member 30 is exposed to a subject side from an opening of a cover member 20 and the first and second protrusions 31 and 32 are formed on this exposed portion. Accordingly, the first and second protrusions 31 and 32 formed on this exposed portion come into contact with a subject (for example, skin of the wrist of a user), when measuring biological information. In FIG. 3A, a detection window of the biological information detection device is configured with the exposed portion of the light transmitting member 30. The light transmitting member 30 is also provided on a portion other than the detection window, that is, a rear side portion of the cover member 20. However, the embodiment is not limited thereto, and the light transmitting member 30 may be provided only on a portion of the detection window.

In the biological information detection device of the embodiment, a pressing force prevention unit 60 which prevents a pressing force applied to a subject (skin of the wrist) by the first protrusion 31 is provided. In FIGS. 3A and 3B, the pressing force prevention unit 60 is provided on a housing surface of the bottom case 304 so as to surround the first and second protrusions 31 and 32 of the light transmitting member 30. Specifically, a surface of the cover member 20 functions as the pressing force prevention unit 60. That is, the pressing force prevention unit 60 (pressing force prevention surface) is formed by molding the surface of the cover member 20 into a banked shape. As shown in FIGS. 5A and 5B, a groove 42 for preventing fluctuation in a pressing force is provided around the first and second protrusions 31 and 32.

It is not necessary to provide the pressing force prevention unit 60 or the groove 42 around whole circumference of the first and second protrusions 31 and 32, and an area where the pressing force prevention unit 60 or the groove 42 is not provided, may be provided around the first and second protrusions 31 and 32.

The light emitting unit 150 irradiates a subject (target) with light and the first and second light receiving units 141 and 142 receive light from a subject. When the light emitting unit 150 emits light and the light is reflected by a subject, for example, the first and second light receiving units 141 and 142 receive the reflected light. The first and second light receiving units 141 and 142 can be realized by light receiving elements such as photodiodes, for example. The light emitting unit 150 can be realized by a light emitting element such as an LED, for example. For example, the first and second light receiving units 141 and 142 can be realized by P-N junction type diode elements which are formed on a substrate of a semiconductor. In this case, it is desirable to form an angle restriction filter for narrowing a light receiving angle or a wavelength restriction filter for restricting a wavelength of light incident to the light receiving element on the diode element.

When a case where the embodiment is applied to the biological information detection device such as a pulsimeter is used as an example, light from the light emitting unit 150 travels the inside of a subject and diffuses or scatters in epidermis, dermis, and hypodermis. After that, the light approaches a blood vessel (portion to be detected) and is reflected. At that time, some light is absorbed by the blood vessel. Since the light absorption ratio in a blood vessel changes due to the effect of the pulse and light intensity of the reflected light also changes, the first and second light receiving units 141 and 142 receive the reflected light and detect a change in the light intensity, and accordingly, it is possible to detect a pulse rate which is biological information. Specifically, as will be described later, when an operation process of biological information of a subject is performed based on a first detection signal detected by the first light receiving unit 141, for example, various processes such as a noise reduction process of the first detection signal can be performed based on a second detection signal detected by the second light receiving unit 142.

A dome-type lens 152 (condensing lens in the broad sense) provided in the light emitting unit 150 in FIG. 4 is a lens for condensing light from an LED chip (a light emitting element chip in the broad sense) which is resin-sealed (sealed by a light transmissive resin) in the light emitting unit 150. That is, in the chip package type (surface mounting type) light emitting unit 150, the LED chip is disposed on the lower portion of the dome-type lens 152, and light from the LED chip is condensed by the dome-type lens 152 and emitted to a subject. Accordingly, the emission efficiency of light to a subject increases and detection sensitivity of the sensor unit 130 can be increased.

The light shielding member 70 is a member for performing shielding of light (unnecessary light). In the embodiment, the light shielding member 70 is provided around (or so as to cover) at least the first and second light receiving units 141 and 142. That is, the light shielding member 70 is not provided on the light emitting unit 150 side, but is provided on the first and second light receiving units 141 and 142 side. For example, the light shielding member 70 is provided around (or so as to cover) the first and second light receiving units 141 and 142 and shields (restricts) unnecessary light from being emitted to the first and second light receiving units 141 and 142. Meanwhile, the light shielding member does not perform shielding for the light emitting unit 150. However, modification can be performed so as to provide the light shielding member 70 on the light emitting unit 150 side.

Figure 7A:
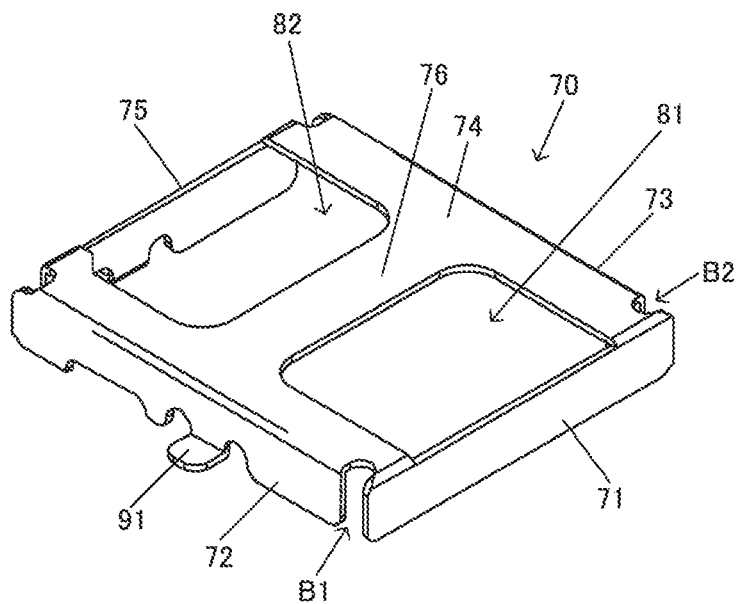
FIGS. 7A and 7B are perspective views showing a specific example of a light shielding member.

Specifically, as shown in FIGS. 7A to 8 will be described later in detail, the light shielding member 70 includes first to third light shielding surfaces 71 to 73 (first to third metal surfaces) and a beam 76, for example. More preferably, the light shielding member 70 is configured with first to fifth shielding surfaces 71 to 75 (first to fifth metal surfaces) and the beam 76. The first light shielding surface 71 functions as a light shielding wall which shields direct light from the light emitting unit 150 from being emitted to the first and second light receiving units 141 and 142. The first light shielding surface 71 (first metal surface) is, for example, provided between the light emitting unit 150 and the first light receiving unit 141. The second and third light shielding surfaces 72 and 73 (second and third metal surfaces) shown in FIGS. 5A and 5B are provided along a direction intersecting (for example, orthogonal to) the first light shielding surface 71. The second and third light shielding surfaces 72 and 73 are light shielding walls on the side surface.

The first opening 81 corresponding to the first light receiving unit 141 is provided with the first to third light shielding surfaces 71, 72, and 73 and the beam 76. That is, the first opening 81 corresponding to the first light receiving unit 141 is provided with the first light shielding surface 71, the beam 76, and eaves (F1, F2, F5, and F6 of FIGS. 5A and 5B).

Specifically, the light shielding member 70 includes a fourth light shielding surface 74 (fourth metal surface). The fourth light shielding surface 74 is provided along a direction intersecting (for example, orthogonal to) the first light shielding surfaces 71 and the second and third light shielding surfaces 72 and 73. The fourth light shielding surface 74 is, for example, a light shielding surface which is the upper surface of the light shielding member 70.

The first and second openings 81 and 82 are formed on the fourth light shielding surface 74 which is the upper surface described above. The first and second openings 81 and 82 are provided with respect to the first and second light receiving units 141 and 142. That is, the fourth light shielding surface 74 includes an outer periphery portion (eaves) coming into contact with the first, second, and third light shielding surfaces 71, 72, and 73 and the beam 76 which extends from the second light shielding surface 72 to the third light shielding surface 73 approximately parallel to light receiving surfaces (RS1 and RS2) of the first light receiving unit 141 or the second light receiving unit 142. Specifically, the first opening 81 formed with the outer periphery portion (eaves) of the fourth light shielding surface 74 and the beam 76 is provided over the first light receiving unit 141 (the side in DR3 direction, that is, a subject side). In addition, the second opening 82 formed with the outer periphery portion (eaves) of the fourth light shielding surface 74 and the beam 76 is provided over the second light receiving unit 142 (the side in DR3 direction, that is, a subject side). The first and second openings 81 and 82 function as apertures which condense light (reflected light or the like) emitted from a subject side in an optical path between a subject and the first and second light receiving units 141 and 142. The fifth light shielding surface 75 (fifth metal surface) which is a light shielding wall of the rear surface is also provided on the light shielding member 70 and shields light emitted from the rear surface side.

It is desirable to perform a reflection prevention process on at least the inner surface of the light shielding member 70. The color of the surface (inner surface or the like) of the light shielding member 70, for example, is set as a predetermined color such as black and prevents diffuse reflection of light. Alternatively, the surface of the light shielding member 70 may have a moth-eye structure. A concave and convex structure of a cycle of several tens to several hundreds of nm is formed on the surface and realizes a reflection prevention structure. When such a reflection prevention process is performed, it is possible to effectively prevent a phenomenon in that the light reflected by the surface of the light shielding member 70 becomes stray light to be a noise component of a detection signal.

The first and second light receiving units 141 and 142 and the light shielding member 70 are mounted on a substrate (160 of FIG. 9A will be described later). The light emitting unit 150 may be mounted on the substrate with the first and second light receiving units 141 and 142 and the light shielding member 70. This substrate is a rigid substrate, for example. A terminal for performing connection with a device side terminal of a signal or a power source of the first and second light receiving units 141 and 142 and the light emitting unit 150 or a terminal for performing connection of a signal or a power source between the terminal and an external main substrate is provided on the substrate described above. For example, as shown in FIGS. 5A and 5B, the device side terminal of the first and second light receiving units 141 and 142 and the terminal of the substrate are connected to each other by wire bonding WL1 and WL2.

In the embodiment, the beam 76 is provided between the first and second openings 81 and 82 of the light shielding member 70. That is, the beam 76 is formed between the first and second openings 81 and 82 functioning as apertures, on the fourth light shielding surface 74 on the upper surface of the light shielding member 70. As shown in FIG. 3B, the beam 76 includes an end portion E1 on the first light receiving unit 141 side and an end portion E2 on the second light receiving unit 142 side. The end portions E1 and E2 are linear end sides. The end portion E1 corresponds to the end side of the first opening 81 on the second light receiving unit 142 side and the end portion E2 corresponds to the end side of the second opening 82 on the first light receiving unit 141 side.

In FIG. 3B, the end portions E1 and E2 of the beam 76 are linear end sides, but may be curved end sides. At least one of the end portions E1 and E2 of the beam 76 may have a curved shape so as to be curved on the second light receiving unit 142 side, for example. At least one thereof may have the same curved shape as that of a boundary 33 of the first and second protrusions 31 and 32 which will be described later. By doing so, it is possible to realize further improvement of strength or an increase in the light intensity of the incident light.

3. Opening and Beam

In the biological information detection device of the embodiment, a surface of the light transmitting member 30 coming into contact with the skin which is a subject is a contact surface having a limited area. A substance which is relatively soft, such as skin, comes into contact with the contact surface of the light transmitting member 30 having a limited area formed of a hard substance such as a resin or glass, for example. By doing so, there is an area which does not come into contact with the skin or an area having weak contact pressure in the vicinity of a rim of the light transmitting member 30, in a viewpoint of mechanics of elasticity. When an external force is applied to a device such as the biological information detection device and the moment is generated in the device, an area in the vicinity of the rim of the contact surface is most easily floated. Regarding light in such an area, irregular intensity of light is easily generated optically due to a change in a dynamic contact state. When the light is incident to the first light receiving unit 141 or the like, noise having no relation to a pulse component may be generated.

Also, in a static contact state, a decrease in signal quality may occur. If the contact surface does not completely come into contact with the skin, outside light which is not from the light emitting unit 150 may be incident to the first light receiving unit 141 or the like. Meanwhile, in a case of the excessive contact pressure, light may penetrate a blood vessel under the skin and a pulsation component is hardly included in the light which has transmitted this area.

As the noise is largely superimposed, signal quality of a pulse wave detection signal may decrease and reliability of measurement data may decrease in various biological measurements such as pulse rate measurement.

Figure 6A:
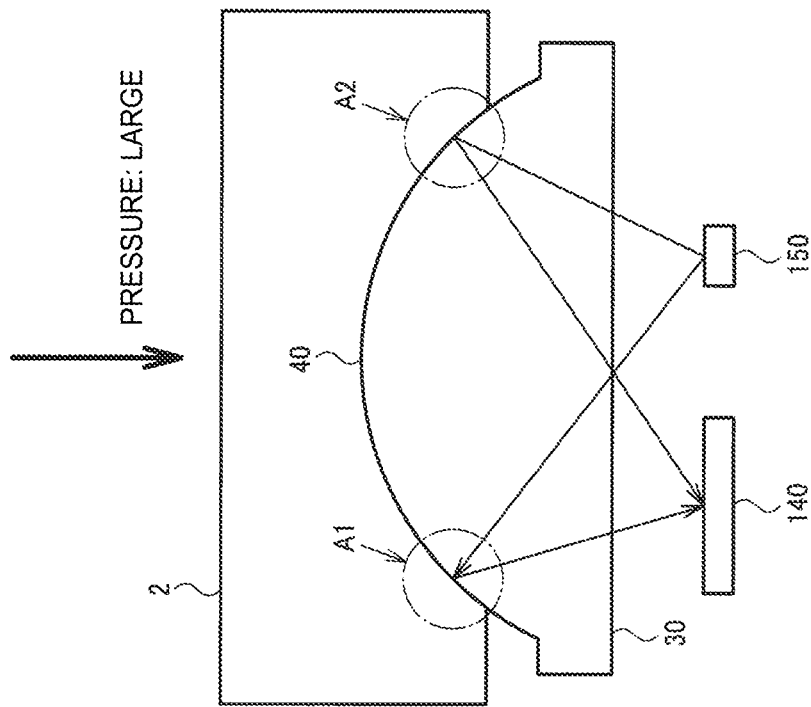
FIGS. 6A and 6B are explanatory diagrams of problems when a pressing force of a light transmitting member against a subject is changed.
Figure 6B:
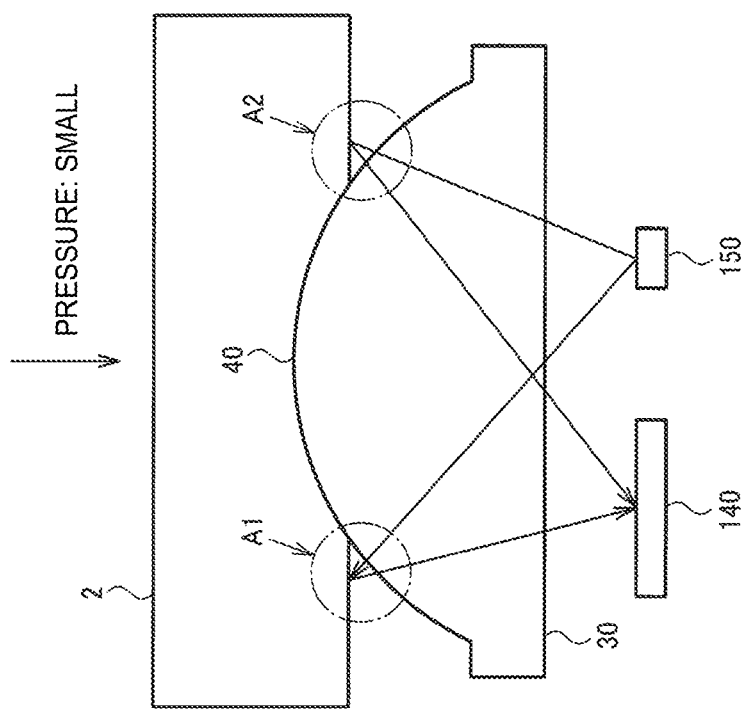

FIG. 6A shows a case where a pressing force of a protrusion 40 (for example, first protrusion 31) of the light transmitting member 30 applied to a skin 2 which is a subject is small and FIG. 6B shows a case where a pressing force thereof is large. When focusing locations shown by A1 and A2 of FIGS. 6A and 6B, a contact state between the skin 2 and the protrusion 40 is changed due to a change in a pressing force. For example, in FIG. 6A, the skin 2 and the protrusion 40 are in a non-contact state or in a slight contact state at the locations of A1 and A2, but the skin and the protrusion are in a contact state, in FIG. 6B. Accordingly, the intensity of light which is emitted from the light emitting unit 150 and returned to the light receiving unit 140 (for example, first light receiving unit 141) may be changed between FIG. 6A and FIG. 6B, and reliability of the measurement data is decreased. That is, a pressing force against the contact surface may be rapidly changed due to a minute change in load at the locations of A1 and A2 of FIG. 6A and FIG. 6B, and reliability of the measurement data may be significantly decreased.

For example, in FIG. 6A and FIG. 6B, the contact surface of the light transmitting member 30 coming into contact with the skin of a human being is configured with a protrusion shape (protrusion) having a curved surface shape. By doing so, a degree of adhesion of the light transmitting member 30 with respect to the skin surface is improved, and therefore, it is possible to prevent penetration of noise light such as reflected light from the skin surface or ambient light.

However, the contact pressure against the skin decreases at the rim (outer periphery) of the protrusion shape, relatively to the center. In this case, when the optimization is performed with the contact pressure at the center, the contact pressure at the rim is smaller than an optimal range. Meanwhile, when the optimization is performed with the contact pressure at the rim, the contact pressure at the center is excessive value with respect to an optimal range.

When the contact pressure is less than the optimal range, body motion noise is superimposed in a pulse wave detection signal due to a case where a pulse wave sensor comes into contact with the skin or is separate from the skin due to shaking of the device or a case where a pulse wave sensor does not completely approach a vein even when the sensor comes into contact with the skin. When the noise component is decreased, it is possible to obtain a pulse wave detection signal having a higher M/N ratio (S/N ratio). Herein, M represents a signal level of a pulse wave detection signal and N represents a noise level.

In order to solve such problems, in the embodiment, as shown in FIGS. 3B to 5B, the first and second openings 81 and 82 are provided on the light shielding member 70. That is, the first and second openings 81 and 82 functioning as apertures are provided so as to condense light, so that light (stray light) is not detected at the locations of A1 and A2 of FIGS. 6A and 6B. The light through the vicinity of the rim of a light transmitting area (for example, protrusion) of the light transmitting member 30 is shielded, while not shielding but transmitting the light passing the center (for example, apex of protrusion) of the light transmitting area of the light transmitting member 30 which is optimally pressed, as much as possible. By doing so, even when the contact state at the locations of A1 and A2 of FIGS. 6A and 6B is changed, the state of light at the locations of A1 and A2 does not affect light receiving results. Accordingly, it is possible to improve reliability of measurement data.

In the embodiment, as shown in FIGS. 3B and 4, the beam 76 is provided between the first light receiving unit 141 and the second light receiving unit 142, in a plan view (plan view from a subject side) in a vertical direction of the light receiving surface RS1 of the first light receiving unit 141. More specifically, in the plan view described above, the beam 76 of the light shielding member 70 is provided between the first opening 81 and the second opening 82. By providing the beam 76, restriction of light incident to the first light receiving unit 141 or the second light receiving unit 142 is performed to receive light necessary for pulse wave measurement as much as possible, the sensitivity or accuracy of the sensor unit 130 is improved, and the strength of the light shielding member 70 or the like can also be ensured.

In the embodiment, the light emitting unit 150 is disposed on the outside of the light shielding member 70, light from the light emitting unit 150 is emitted to the skin of the wrist, and the reflected light having information regarding a blood flow is incident to the first light receiving unit 141 to measure the pulse. Since the light directly emitted from the light emitting unit 150 does not have information regarding a blood flow, it is necessary to shield this light because this light may cause a decrease in sensitivity. As illustrated in FIG. 10 or the like will be described later, the second light receiving unit 142 receives information of light emitted through the second protrusion 32 having curvature different from that of the first protrusion 31 on the first light receiving unit 141 side, in order to receive information for removing a noise signal. Some light incident to the second light receiving unit 142 side may also be incident to the first light receiving unit 141 side and this causes a decrease in sensitivity, and accordingly, it is necessary to shield such light. The end portion E1 (end surface) of the beam 76 of the embodiment on the first light receiving unit 141 side is provided at a location for shielding the light.

Meanwhile, it is necessary to ensure a width of the beam 76 in order to ensure the strength of the beam 76. However, all of light which is incident more than a given angle from the curvature of the first protrusion 31 from the light incident to the second light receiving unit 142 side from the first protrusion 31 is reflected and is not emitted to the second light receiving unit 142. Accordingly, by setting the other end portion E2 (end surface) of the beam 76 to be close to the second light receiving unit 142 side as close as possible, it is possible to ensure the strength of the beam 76 while ensuring the light intensity of the light incident to the second light receiving unit 142. In the embodiment, for example, a width of the beam 76 can be set to be equal to or greater than 1.1 mm and sufficient strength thereof can be ensured.

For example, as a method of a comparative example of the embodiment, a method of not providing the beam 76 and providing only one opening for the first and second light receiving units 141 and 142 is considered.

However, in the method of the comparative example, the light emitted through the second protrusion 32 of the light transmitting member 30 may be incident to the first light receiving unit 141 and detection sensitivity or detection accuracy may be decreased.

In this viewpoint, in the embodiment, the beam 76 is provided and openings are divided into the first opening 81 for the first light receiving unit 141 and the second opening 82 for the second light receiving unit 142. Accordingly, by shielding the light emitted through the second protrusion 32 of the light transmitting member 30 by the beam 76, it is possible to prevent light emission to the first light receiving unit 141 and to effectively prevent a decrease in detection sensitivity or detection accuracy.

In the method of the comparative example, since one opening having a large area is formed on the upper surface of the light shielding member 70, sufficient strength of the light shielding member 70 may not be ensured. Particularly, as will be described later, when the light shielding member 70 is formed by performing sheet metal working of metal, a thickness of each light shielding surface (metal surface) of the light shielding member 70 is decreased and it is more difficult to ensure the strength thereof. Accordingly, the light shielding member 70 may be deformed when mounting the light shielding member 70 to the substrate of the sensor unit 130, for example, or any external force may be applied to the light shielding member 70 when using the biological information detection device and the light shielding member 70 may be deformed.

In this viewpoint, according to the embodiment, since the beam 76 is provided between the first opening 81 (first light receiving unit 141) and the second opening 82 (second light receiving unit 142), it is possible to ensure the strength of the light shielding member 70 by the beam 76. For example, it is also easy to ensure the strength of the fourth light shielding surface 74 or the like which is the upper surface of the light shielding member 70. Particularly, in the embodiment, the end portion E2 of the beam 76 is set to be close to the second light receiving unit 142 side (LE2<LE1), by focusing that the curvature of the first protrusion 31 is greater than that of the second protrusion 32. By doing so, it is possible to increase the width of the beam 76 and to further increase the strength thereof.

Next, the light shielding structure of the embodiment will be described with reference to FIGS. 4 to 5B in more detail. In FIG. 4, the first light receiving unit 141 and the second light receiving unit 142 are disposed along the first direction DR1. The first light receiving unit 141 is disposed on the side of the first direction DR1 of the light emitting unit 150, for example, and the second light receiving unit 142 is disposed on the side of the first direction DR1 of the first light receiving unit 141. Herein, the first direction DR1 is a direction along the surface (housing surface of the bottom case) of the cover member 20 of FIG. 3A, for example. Alternatively, the first direction DR1 is a direction from the light emitting unit 150 towards the first light receiving unit 141, a direction from the first light receiving unit 141 towards the second light receiving unit 142, or a direction from the light emitting unit 150 towards the second light receiving unit 142. The second direction DR2 is a direction opposite to the first direction DR1. The third direction DR3 is a direction intersecting (orthogonal to) the first direction DR1, for example. Alternatively, the third direction DR3 is a direction vertical to the light receiving surface RS1 of the first light receiving unit 141, a direction parallel to an optical axis of the light emitting unit 150, or a direction vertical to the light receiving surface RS2 of the second light receiving unit 142. The fourth direction DR4 is a direction opposite to the third direction DR3. That is, the third direction DR3 is a direction from the biological information detection device towards a subject at the time of mounting of the biological information detection device and the fourth direction DR4 is a direction from a subject to the biological information detection device.

In FIG. 4, a distance between the end portion E1 (end surface) of the beam 76 on the first light receiving unit 141 side and the end portion E3 (end surface) of the first light receiving unit 141 on the second light receiving unit 142 side in the first direction DR1 is set as LE1. The distance LE1 is a distance between the end portion E1 of the beam 76 and the end portion E3 of the first light receiving unit 141 in a plan view seen from the subject side, for example. In addition, a distance between the end portion E2 (end surface) of the beam 76 on the second light receiving unit 142 side and the end portion E4 of the second light receiving unit 142 on the first light receiving unit 141 side in the first direction DR1 is set as LE2. The distance LE2 is a distance between the end portion E2 of the beam 76 and the end portion E4 of the second light receiving unit 142 in a plan view seen from the subject side, for example.

In this case, a relationship of LE1>LE2 is satisfied, in FIG. 4. For example, in a plan view seen from the subject side, the distance between the end portion E1 of the beam 76 and the first light receiving unit 141 is long and the distance between the end portion E2 of the beam 76 and the second light receiving unit 142 is short. That is, the beam 76 is provided from a center position between the first light receiving unit 141 and the second light receiving unit 142, to a position shifted to the second light receiving unit 142 side, that is, a position biased to the second light receiving unit 142 side. For example, the distance LE1 is set as a distance so that the light emitted from the second protrusion 32 side is not incident to the first light receiving unit 141 (light receiving surface RS1) by light shielding of the beam 76. Meanwhile, when a noise removing process of the first detection signal of the first light receiving unit 141 is performed based on the second detection signal of the second light receiving unit 142, as will be described later, the emission of the light emitted from the first protrusion 31 side to the second light receiving unit 142 (light receiving surface RS2) is permitted. However, since the curvature of the first protrusion 31 is large (radius of curvature is small), there is a total reflection area of the incident light and the incident light in this total reflection area is not incident to the second light receiving unit 142. Accordingly, the width of the beam 76 increases by setting the distance LE2 shorter than the total reflection area so as to permit only the incident light at the position of the second light receiving unit 142 side (second protrusion 32 side), and therefore, the strength of the beam 76 is ensured. For example, a relationship of LE1>1.5×LE2 is obtained. For example, in FIG. 4, LE1 is, for example, from 0.30 mm to 0.50 mm and is, for example, approximately 0.425 mm. The LE2 is from 0.13 mm to 0.30 mm and is, for example, approximately 0.235 mm. The width of the beam 76 is from 1.0 mm to 1.2 mm and is, for example, approximately 1.1 mm. The height of the beam 76 from the substrate is from 0.70 to 1.0 mm and is, for example, approximately 0.85 mm. In FIG. 4, the distance (distance between center positions) between the light emitting unit 150 and the first light receiving unit 141 is, for example, from 1.0 mm to 3.0 mm and is, for example, approximately 2 mm. The distance (distance between center positions) between the light emitting unit 150 and the second light receiving unit 142 is, for example, from 4.6 mm to 6.6 mm and is, for example, approximately 5.6 mm.

In FIG. 4, an area between end portions E5 and E6 is a light receiving area RS1 of the first light receiving unit 141 and an area between end portions E7 and E8 is a light receiving area RS2 of the second light receiving unit 142. In the first and second light receiving units 141 and 142, the light receiving elements are provided in the light receiving areas RS1 and RS2 and the light receiving areas are areas in which the incident light is received to output a detection signal. For example, the light receiving areas RS1 and RS2 are disposition areas of P-N junction diode elements formed on the substrate of the semiconductor.

The light transmitting member 30 includes the first protrusion 31 and the second protrusion 32. The sectional shape of the first protrusion 31 and the second protrusion 32 is a curved shape and the curvature of the first protrusion 31 is greater than the curvature of the second protrusion 32. That is, a radius of curvature of the first protrusion 31 is smaller than a radius of curvature of the second protrusion 32. The first protrusion 31 is a protrusion which is more protruded to the subject side, compared to the second protrusion 32. That is, when a height (height of apex of curved surface shape of protrusion) of the first protrusion 31 from the substrate (substrate where the light emitting unit and the light receiving units are mounted) is set as HA1 and a height (height of apex of curved surface shape of protrusion) of the second protrusion 32 is set as HA2, a relationship of HA1>HA2 is satisfied.

The boundary 33 of FIG. 4 is a boundary between the first protrusion 31 and the second protrusion 32 and is a portion where the curved surface of the light transmitting member 30 (curved surfaces of the first and second protrusions 31 and 32) is not continued. As shown in FIG. 3B, the boundary 33 has a curved shape which is curved to the second light receiving unit 142 side, in a plan view seen from the subject side. For example, the boundary 33 has an arc shape (approximately arc shape) having the center of curvature on the first light receiving unit 141 side, in a plan view seen from the subject side.

In the embodiment, the beam 76 of the light shielding member 70 shields the light so that the light passing through the boundary 33 between the first protrusion 31 and the second protrusion 32 is not incident to the light receiving surface RS1 of the first light receiving unit 141. For example, as shown in FIG. 4, light beams LT1 and LT2 emitted to the first protrusion 31 side without passing the boundary 33 are not shielded by the beam 76 and are incident to the light receiving surface RS1 of the first light receiving unit 141. By doing so, it is possible to detect pulse wave information contained in the light beams LT1 and LT2.

Meanwhile, the light passing the boundary 33 is shield by the beam 76 and so as not to incident to the light receiving surface RS1 of the first light receiving unit 141. That is, the beam 76 is positioned on an optical path (on an optical path determined by a refractive index of the light transmitting member 30) of the light passing the boundary 33. For example, the beam 76 may be positioned on a line connecting the boundary 33 and the end portion E5 of the light receiving surface RS1. In addition, light passing a position (position on the second protrusion 32 side or a position on the side of the first direction DR1) on the second light receiving unit 142 without passing the boundary 33 is also shielded by the beam 76 so as not to incident to the light receiving surface RS1 of the first light receiving unit 141. By doing so, the light passing the second protrusion 32 for the second light receiving unit 142 is not incident to the light receiving surface RS1 of the first light receiving unit 141, and accordingly, noise light is reduced and detection sensitivity or detection accuracy can be improved.

In FIG. 4, the beam 76 of the light shielding member 70 is positioned at a position where light beams LT3 and LT4 which pass a position (position on the second protrusion 32 side or position on the side of the first direction DR1) on the second light receiving unit 142 without passing a total reflection boundary BT of the first protrusion 31 and incident to the end portion E7 (in the broad sense, a point of the light receiving surface RS2 which is closest to the beam 76) of the light receiving surface RS2 of the second light receiving unit 142 on the first light receiving unit 141 side are not shielded.

That is, since the curvature of the first protrusion 31 is large and light passing the position on the first light receiving unit 141 side without passing the total reflection boundary BT is totally reflected by the surface of the first protrusion 31 and does not penetrate the inside of the light transmitting member 30, the light is not incident to the light receiving surface RS2 of the second light receiving unit 142. Accordingly, the width of the beam 76 is increased and the ensuring of the strength is prioritized. The light beams LT3 and LT4 are not shielded by the beam 76 and are incident to the light receiving surface RS2 of the second light receiving unit 142, so as to ensure the incident light intensity of the second light receiving unit 142.

By disposing and setting the beam 76 as described above, it is possible to ensure the strength of the light shielding member 70 while improving detection sensitivity or detection accuracy of the biological information detection device.

θ (for example, θ=approximately 60 degrees) in FIG. 4 shows a light receiving range of the light incident to the first and second light receiving units 141 and 142, when an angle restriction filter for restricting an angle of incidence of light incident to the light receiving area of the first and second light receiving units 141 and 142 is provided. For example, regarding light beams LT5 and LT6 in the light receiving range, the light intensity is not decreased by the angle restriction filter and light beams are incident to the first and second light receiving units 141 and 142 at the appropriate light intensity, and information thereof is appropriately detected. Meanwhile, the light intensity of the light beyond the light receiving range is sufficiently decreased by the angle restriction filter.

The direct light beam LT7 incident from the light emitting unit 150 without passing a subject is shielded by the first light shielding surface 71 of the light shielding member 70 and is not incident to the first light receiving unit 141 or the like. The first light shielding surface 71 functions as a light shielding wall which is provided on the light emitting unit 150 and the first light receiving unit 141. The light emitting unit 150 includes the dome-type lens 152 and has a large height from the substrate. Accordingly, the height of the first light shielding surface 71 is set as a height so as to shield the direct light from the light emitting unit 150. A light beam LT8 emitted from the side in the opposite direction (rear side) of the light emitting unit 150 is also shielded by the fifth light shielding surface 75 of the light shielding member 70.

FIGS. 5A and 5B are sectional views in a direction orthogonal to the first direction DR1 of FIG. 4. FIG. 5A is a sectional view at a position of the first light receiving unit 141 and FIG. 5B is a sectional view at a position of the second light receiving unit 142.

F1 and F2 of FIG. 5A are formed as eaves (outer periphery) of the upper surface of the light shielding member 70 so that light beams LT9 and LT10 passing a discontinuous boundary (discontinuous surface) of the light transmitting member 30 shown as F3 and F4 are not incident to the light receiving surface RS1 of the first light receiving unit 141, and the light beams LT9 and LT10 are shielded. By doing so, negative effects on the light beams LT9 and LT10 passing the discontinuous boundary are reduced and detection sensitivity or detection accuracy can be improved. In the same manner as described above, F5 and F6 of FIG. 5B are formed as eaves (outer periphery) of the upper surface of the light shielding member 70 so that light beams LT11 and LT12 passing a discontinuous boundary (discontinuous surface) of the light transmitting member 30 shown as F7 and F8 are not incident to the light receiving surface RS2 of the second light receiving unit 142, and the light beams LT11 and LT12 are shielded.

As shown as F9 of FIG. 5A, a chamfer is provided on the inner corner of the light transmitting member 30. Accordingly, it is possible to wide a width LF of the light transmitting member 30 at that portion and to ensure the strength or the like of the light transmitting member 30. In the same manner as described above, as shown as F10 of FIG. 5A and F11 and F12 of FIG. 5B, a chamfer is provided on the inner corner of the light transmitting member 30 and the strength or the like is ensured.

4. Sheet Metal Working

Figure 7B:
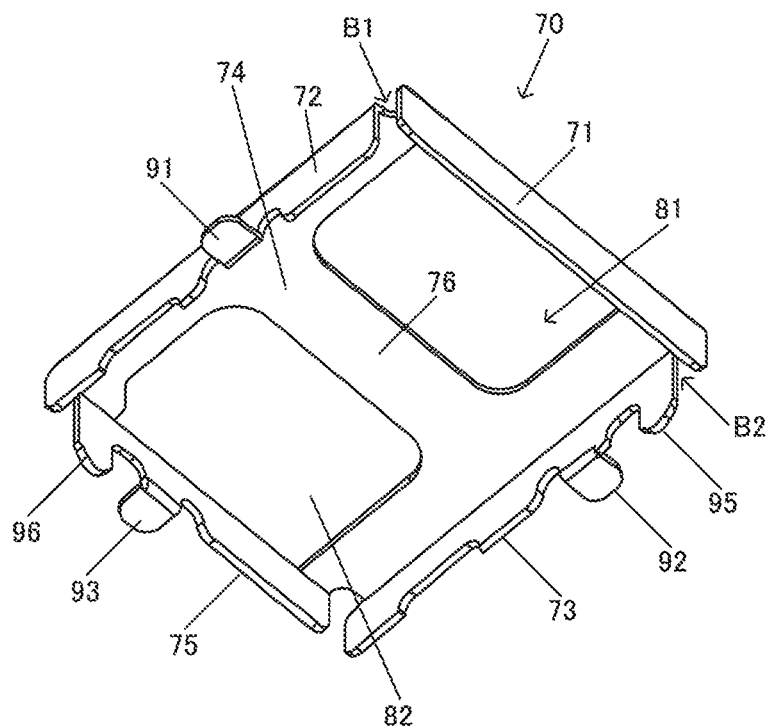

In the embodiment, the light shielding member 70 is formed by performing sheet metal working of metal (for example, an alloy of tin and copper), for example. The light shielding member 70 having a shape shown in FIGS. 7A, 7B, and 8 is formed by performing sheet metal working for one metal sheet, for example. Herein, FIG. 7A is a perspective view when the light shielding member 70 is seen upward obliquely and FIG. 7B is a perspective view when the light shielding member 70 is seen downward obliquely. FIG. 8 is a plan view, a side view, a front view, and a rear view showing a specific example of the light shielding member 70.

The light shielding member 70 includes the first to third light shielding surfaces 71, 72, and 73. The first to third light shielding surfaces 71, 72, and 73 are metal surfaces formed by the sheet metal working. The first light shielding surface 71 is provided between the light emitting unit 150 and the first light receiving unit 141. That is, when the light emitting unit 150, the first and second light receiving units 141 and 142, and the light shielding member 70 are mounted on the substrate, the first light shielding surface 71 is positioned between the light emitting unit 150 and the first light receiving unit 141. For example, the first light shielding surface 71 is alight shielding wall including a wall surface along a direction intersecting (orthogonal to) a line connecting a center position of the light emitting unit 150 and a center position of the first light receiving unit 141. The emission of the direct light from the light emitting unit 150 to the first light receiving unit 141 is prevented by the first light shielding surface 71 which is a light shielding wall.

The second and third light shielding surfaces 72 and 73 are provided so as to intersect (to be orthogonal to) the first light shielding surface 71. When the first light shielding surface 71 is a surface on the front side, the second and third light shielding surfaces 72 and 73 are surfaces on a side surface side and are light shielding walls on the side surface side.

The first light shielding surface 71 and the second light shielding surface 72 are provided so as to be adjacent to each other with a first gap area shown as B1 of FIGS. 7A and 7B interposed therebetween. The first light shielding surface 71 and the third light shielding surface 73 are provided so as to be adjacent to each other with a second gap area shown as B2 interposed therebetween.

The light shielding member 70 includes fourth and fifth light shielding surfaces 74 and 75. The fourth light shielding surface 74 is a light shielding surface which is the upper surface of the light shielding member 70. The first and second openings 81 and 82 which function as apertures for condensing light (reflected light or the like) from a subject in the optical path of the first and second light receiving units 141 and 142 as described above, are formed on the fourth light shielding surface 74. The fifth light shielding surface 75 is a metal surface which is a light shielding wall of the rear surface and shields light emitted from the rear side.

As described above, in the embodiment, the light shielding member 70 for shielding the first light receiving unit 141 from external light is provided. The light shielding member 70 is formed by performing sheet metal working of metal and a light shielding wall between the light emitting unit 150 and the first light receiving unit 141 is realized by, for example, the light shielding surface 71 of the light shielding member 70.

For example, as a distance between the light emitting unit 150 and the first light receiving unit 141 is short, optical efficiency and performance of the sensor unit 130 of the biological information detection device are improved. For example, the optical efficiency and performance decrease in inverse proportion to square of the distance. Accordingly, it is desired to set the distance between the light emitting unit 150 and the first light receiving unit 141 to be short as much as possible.

Meanwhile, when the distance between the light emitting unit 150 and the first light receiving unit 141 is shortened, the direct light from the light emitting unit 150 is incident to the first light receiving unit 141, a DC component may be increased and performance may be deteriorated. Accordingly, in the embodiment, the light shielding surface 71 which is a light shielding wall is provided between the light emitting unit 150 and the first light receiving unit 141.

In this case, as a method of a comparative example of the embodiment, a method of forming the light shielding member 70 by mold injection is considered. A method of a comparative example using the mold injection is an advantageous method in a viewpoint of mass productivity of the device.

However, when the light shielding member 70 is formed by mold injection, a wall thickness of the light shielding surface 71 may be increased. That is, when the wall thickness of the light shielding surface 71 is set to be small, a part of the light shielding surface 71 may not be sufficiently filled with a resin at the time of mold injection and it is difficult to realize the light shielding surface 71 having sufficient strength. Accordingly, in a method of a comparative example using the mold injection, a thickness of the light shielding surface 71 which is a light shielding wall may be, for example, equal to or greater than 0.4 mm.

When the light shielding surface 71 is thick as described above, the distance between the light emitting unit 150 and the first light receiving unit 141 may also be increased. Accordingly, the length of the optical path between the light emitting unit 150 and the first light receiving unit 141 through a subject may be increased, for example, and the optical efficiency and performance of the sensor unit 130 may be deteriorated.

Therefore, in the embodiment, the light shielding member 70 is formed by the sheet metal working of metal. For example, by folding one metal sheet by the sheet metal working, the light shielding member 70 formed of the light shielding surfaces 71, 72, 73, 74, and 75 is formed. Specifically, the light shielding member 70 is formed by folding the light shielding surfaces 71, 72, 73, and 75 at a right angle (approximately right angle) with respect to the light shielding surface 74 which is the upper surface.

The light shielding surface 71 opposing the light emitting unit 150 is a light shielding wall which shields emission of the direct light from the light emitting unit 150 to the first light receiving unit 141. The first and second openings 81 and 82 condensing light from a subject (target) in the optical path between a subject and the first light receiving unit 141 are provided on the light shielding surface 74 which is the upper surface.

As described above, when the light shielding wall is realized using the light shielding surface 71 by the sheet metal working, it is possible to decrease the thickness of the light shielding wall compared to a method of the comparative example using mold injection. In a case of using the sheet metalworking, for example, even when the thickness of the metal surface is, for example, approximately 0.1 mm, it is possible to realize the light shielding member 70 having sufficient strength. Accordingly, the thickness of the light shielding surface 71 which is a light shielding wall can also be approximately 0.1 mm. Accordingly, compared to a method of the comparative example using mold injection in which the thickness of the light shielding wall becomes equal to or greater than 0.4 mm, for example, it is possible to sufficiently decrease the thickness of the light shielding wall and also to shorten the distance between the light emitting unit 150 and the first light receiving unit 141 by the amount of the decreased thickness. Therefore, it is also possible to shorten the length of the optical path of light from the light emitting unit 150 to the first light receiving unit 141 through a subject while preventing the emission of the direct light from the light emitting unit 150 to the first light receiving unit 141 by the light shielding surface 71, and thus, it is possible to improve detection performance or the like of the sensor unit 130.

Particularly, in FIG. 4, the chip package type light emitting unit 150 is used. In the chip package type light emitting unit 150, the dome-type lens 152 is disposed on an LED chip, for example, and accordingly, emission efficiency of light to a subject can be increased and detection sensitivity of the sensor unit 130 can be increased.

However, an occupation area of the disposition of the chip package type light emitting unit 150 is great, compared to a case of a type realized by disposing an LED chip on a reflector, for example. Accordingly, the distance between the light emitting unit 150 and the first light receiving unit 141 may be increased by that amount. In this viewpoint, according to the embodiment, since the thickness of the light shielding surface 71 can be sufficiently decreased as described above, it is possible to cope with a case using the chip package type light emitting unit 150, and it is possible to improve detection performance such as detection sensitivity.

In the embodiment, the light shielding member 70 is not provided on the light emitting unit 150 side, but is provided on the first and second light receiving units 141 and 142 side. That is, the light shielding member 70 covers the first and second light receiving units 141 and 142 to perform the light shielding thereof, but does not cover the light emitting unit 150.

For example, when the light shielding member 70 has a shape so as to shield the light emitting unit 150 as well, some light from the light emitting unit 150 towards a subject is shielded by the light shielding member 70, the intensity of light emitted to a subject is decreased, and detection performance such as detection sensitivity may be decreased.

In this viewpoint, when the shape of the light shielding member 70 is set as a shape so as to shield only the first and second light receiving units 141 and 142, it is possible to prevent occurrence of a phenomenon in that the light emitted from the light emitting unit 150 is shielded by the light shielding member 70 and the light intensity of the light to a subject is decreased.

The configuration of not providing the light shielding member 70 on the light emitting unit 150 side but providing only on the first and second light receiving units 141 and 142 side is an advantageous configuration, in order to decrease the thickness of the sensor unit 130. For example, as shown in FIG. 4, the light emitting unit 150 including the dome-type lens 152 has a height higher than that of the first and second light receiving units 141 and 142. Accordingly, when the light shielding member 70 is provided on the light emitting unit 150 side, the height thereof on the light emitting unit 150 side is increased by that amount and this becomes disturbance of the thin thickness of the sensor unit 130.

In this viewpoint, when the configuration of providing the light shielding member 70 only on the first and second light receiving units 141 and 142 is used, there is no light shielding member 70 on the light emitting unit 150 side, and accordingly, it is possible to make the height on the first and second light receiving units 141 and 142 and the height on the light emitting unit 150 side to be the same, as shown in FIG. 4, for example. Therefore, it is possible to decrease the height of the entire sensor unit 130 and the thin sensor unit 130 is easily realized, compared to a method of providing the light shielding member 70 even on the light emitting unit 150 side.

When the light shielding member 70 is formed by the sheet metal working, a gap area is provided between the light shielding surface 71 and the light shielding surface 72 adjacent to each other, as shown as B1 of FIGS. 7A and 7B or C1 of FIG. 8. In addition, a gap area is provided between the light shielding surface 71 and the light shielding surface 73 adjacent to each other, as shown as B2 of FIGS. 7A and 7B or C2 of FIG. 8. Further, a gap area is also provided between the light shielding surface 75 and the light shielding surfaces 72 and 73. If such a gap area is not provided, when the light shielding surfaces 71, 72, 73, and 75 are folded with respect to the light shielding surface 74 which is the upper surface by the sheet metal working, distortion may occur in the folded part and folding processing may not be excellently performed.

In a viewpoint, when the gap area is provided as shown as B1 and B2 of FIGS. 7A and 7B or C1 and C2 of FIG. 8 and the folded corner portion of the metal surface has a folded shape (R shape), for example, it is possible to prevent occurrence of problems described above.

Figure 9A:
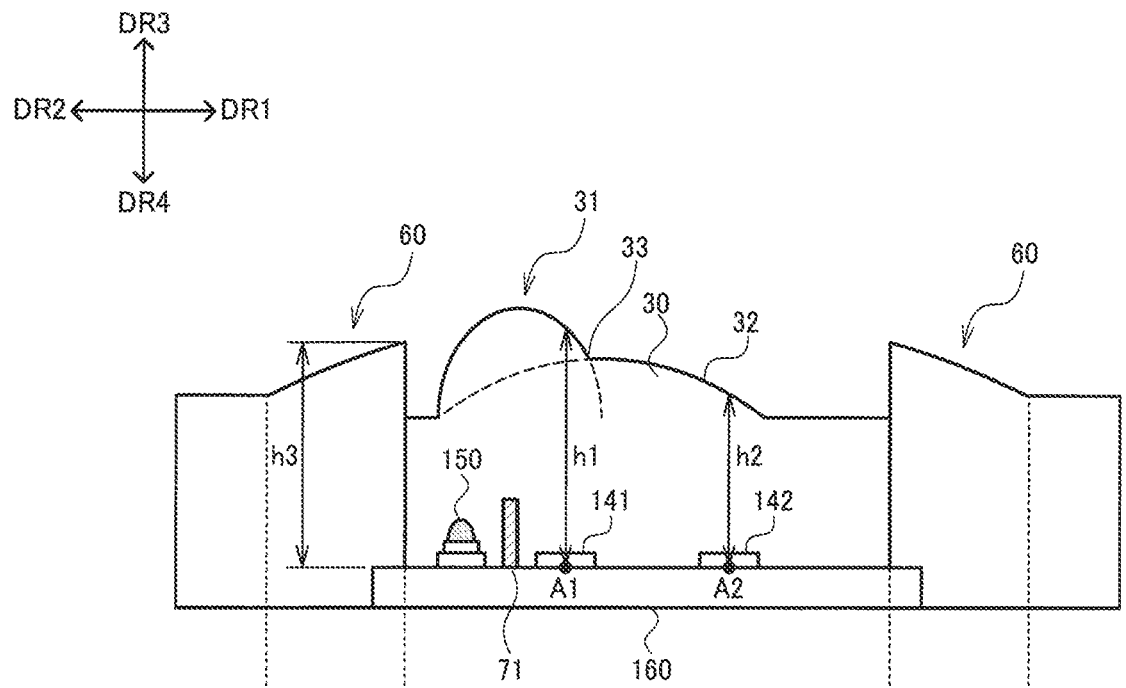
FIGS. 9A and 9B are a sectional view and a plan view of a sensor unit for illustrating a setting method of a height of the light transmitting member.

The first and second light receiving units 141 and 142 and the light shielding member 70 of the sensor unit 130 are mounted on the substrate (160 of FIG. 9A). The light emitting unit 150 may be configured so as to be mounted on the substrate with the first and second light receiving units 141 and 142. As shown in FIGS. 7A to 8, the light shielding member 70 includes protrusions 91, 92, and 93. The protrusion 91 is formed to be folded so as to be protruded to the outer side (direction from the inner side of the light shielding member 70 towards the outside) from the light shielding surface 72 which is one side surface of the light shielding member 70. The protrusion 92 is formed to be folded so as to be protruded to the outer side from the light shielding surface 73 which is the side surface. The protrusion 92 is formed to be folded so as to be protruded to the outer side from the light shielding surface 73 which is the rear surface.

The light shielding member 70 includes the protrusions 95 and 96 for fixing the light shielding member 70 to the substrate. The protrusion 95 is formed to be protruded downwards (direction towards the substrate) from the light shielding surface 73. The protrusion 96 is formed to be protruded downwards (direction towards the substrate) from the light shielding surface 75. The protrusions 95 and 96 are locked on a hole formed on the substrate and accordingly the light shielding member 70 is fixed to the substrate.

As shown in FIG. 8, the protrusions 91, 92, and 93 are provided so that attachment surfaces of the protrusions 91, 92, and 93 are positioned at a distance from an installation surface of the substrate on which the light shielding member 70 is attached to a height HB (HB>0). For example, the protrusions 91, 92, and 93 are formed to be folded in an L shape by the sheet metal working, so that the lower surface which is the attachment surfaces of the protrusions 91, 92, and 93 is positioned at a distance from the upper surface which is the installation surface of the substrate to the height HB. HB is, for example, approximately 0.05 mm.

An adhesive is applied to the lower surface of the protrusions 91, 92, and 93 in a manufacturing step of the sensor unit 130, for example. The light shielding member 70 is attached to the substrate, by inserting the protrusions 95 and 96 to the hole of the substrate. By doing so, it is possible to attach and fix the light shielding member 70 to the substrate with an adhesive applied to the lower surface of the protrusions 91, 92, and 93, while positioning by inserting the protrusions 95 and 96 to the hole of the substrate.

In this case, in the embodiment, a distance between the attachment surface (lower surface) of the protrusions 91, 92, and 93 and the installation surface (upper surface) of the substrate satisfies HB>0. Accordingly, even when an adhesive is applied to the attachment surface of the protrusions 91, 92, and 93, the attachment surface (lower surface) which is an end surface of the light shielding surfaces 71 to 75 on the substrate side, for example, can be adhered to the installation surface (upper surface) of the substrate. Therefore, it is possible to prevent variation in height of the light shielding member 70 after attachment and fixation with an adhesive, and the thickness of the device is easily decreased.

5. Reduction of Body Motion Noise

When biological information such as pulse wave information is detected using the photoelectric sensor (sensor unit), noise due to body motion may be generated. Accordingly, in order to detect biological information with excellent accuracy, it is necessary to reduce body motion noise by any method.

When reducing the body motion noise, a component corresponding to a pulse signal is maintained as much as possible among detection signals of the photoelectric sensor and a component corresponding to the body motion noise is reduced (in the narrow sense, removed). That is, in the reduction process of the body motion noise, it is necessary to recognize a signal component corresponding to the body motion noise.

With respect to this, a method of reducing the body motion noise using a motion sensor such as an acceleration sensor is known. Since the motion sensor is a sensor which detects motion of a user (wearer of the biological information detection device), a signal corresponding to the body motion, that is, a signal corresponding to the body motion noise can be acquired using the motion sensor.

In the embodiment, it is possible to use a method of reducing the body motion noise using the motion sensor, but in the embodiment, a method of obtaining a signal containing lots of body motion noise items by preparing the second light receiving unit 142 which is separate from the first light receiving unit 141 which detects a pulse signal is used.

As described above, the body motion noise items are contained in the detection signal in the photoelectric sensor. By using this point, by setting the sensitivity of the pulse signal low and the sensitivity of the body motion noise high in the second light receiving unit 142, it is possible to obtain a detection signal mainly containing body motion noise.

When a signal corresponding to the body motion noise is detected in the second light receiving unit 142, it is possible to reduce the body motion noise by removing (reducing) components corresponding to the detection signal in the second light receiving unit 142 from the detection signals in the first light receiving unit 141. At that time, since the sensitivity of the pulse signal is low in the second light receiving unit 142, it is possible to prevent excessive decrease of the pulse components contained in the detection signal of the first light receiving unit 141.

However, in order to perform the process, it is desired to set the characteristics (for example, frequency characteristics) of the body motion noise contained in the detection signal between the first light receiving unit 141 and the second light receiving unit 142 to coincide with each other or to be sufficiently close to each other. That is, the first light receiving unit 141 mainly detects the pulse signal and the second light receiving unit 142 maintains high correlation of detection signals of the two light receiving units, while maintaining a difference in the detection characteristics so as to mainly detect the body motion noise.

For example, in the method disclosed in JP-A-2013-176535, frequency bands of light detected in the plurality of light receiving units are largely different from each other. Accordingly, although it is possible to have different characteristics of the detection signals in each light receiving unit, it is difficult to maintain a correlation in some extent. This is because, if the wavelengths of light are different, a penetration depth into a living body is different, and a structure of a blood vessel or a bone which is a detection target is also different.

Accordingly, in the embodiment, the wavelength bands of light used are set to be the same as each other, for example, in the first and second light receiving units 141 and 142. The light having the same wavelength bands does not mean that the wavelengths at the maximum strength are completely the same, but means that the wavelengths at the maximum strength are in a predetermined range (for example, range of the same color). The light output by the light emitting unit 150 is light at a wavelength band contained in a range of 470 nm to 610 nm, for example. More specifically, the light output by the light emitting unit 150 is light at a wavelength band contained in a range of 520 nm to 570 nm. This light at a wavelength band is easily reflected by hemoglobin in a blood vessel, compared to other wavelengths.

Hereinafter, a specific configuration of the sensor unit 130 in that a correlation of some extent is maintained for the detection signals in each light receiving unit as described above and requirement of different characteristics is satisfied will be described. As will be described later with reference to FIGS. 11 to 15, it is found that the sensitivity with respect to the pulse signal or the sensitivity with respect to the body motion noise changes depending on a pressing force applied to a subject or a distance between the light emitting unit and the light receiving unit. The pressing force applied to a subject can be adjusted by a position corresponding to the light receiving unit or a height of the light transmitting member which comes into contact with a subject.

That is, hereinafter, a method of setting the height of the light transmitting member in a position or area corresponding to the light receiving unit and distance between the light emitting unit and the light receiving unit or a specific configuration of the sensor unit 130 having the height and distance appropriately set by the method will be described.

Figure 9B:
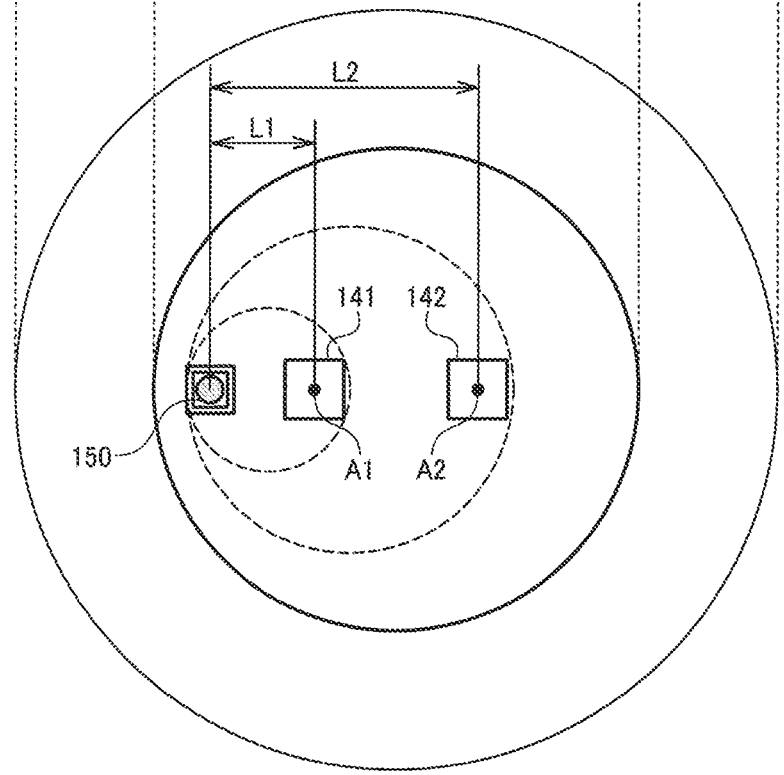

For example, FIG. 9A is a sectional view of the sensor unit 130 and FIG. 9B is a plan view showing disposition of the light emitting unit 150 and the first and second light receiving units 141 and 142 on the substrate 160. FIG. 9B corresponds to a plan view when the components are observed in a direction (DR4) from a subject in the mounted state to the biological information detection device in FIG. 9A. That is, FIG. 9B corresponds to a plan view when the components are observed in a direction from the first light receiving unit 141 or the second light receiving unit 142 towards the substrate 160, in a direction orthogonal to the light receiving area (light receiving surface) of the first light receiving unit 141 or the second light receiving unit 142. FIGS. 9A and 9B schematically show the configuration (particularly, height or shape of the light transmitting member 30) of the sensor unit 130 of the embodiment, for convenience of drawings, and dimensions or ratios in the drawings are different to actual dimensions or ratios.

In the embodiment, as shown in FIGS. 9A and 9B, in the direction (DR3) from the biological information detection device to a subject, when a height of the light transmitting member 30 in a position or an area corresponding to the first light receiving unit 141 is set as h1 and a height of the light transmitting member 30 in a position or an area corresponding to the second light receiving unit 142 is set as h2, a relationship of h1>h2 is set.

At this time, the biological information detection device of the embodiment can include the processing unit 200 which operates biological information of a subject, based on the first detection signal detected by the first light receiving unit 141, as will be described later with reference to FIG. 10. By doing so, it is possible to perform the operation of the biological information such as a pulse using the first detection signal from the first light receiving unit 141.

In the biological information detection device of the embodiment, when a distance between the light emitting unit 150 and the first light receiving unit 141 is set as L1 and a distance between the light emitting unit 150 and the second light receiving unit 142 is set as L2, a relationship of L1<L2 is satisfied, as shown in FIG. 9B. That is, the first light receiving unit 141 is disposed between the light emitting unit 150 and the second light receiving unit 142. The processing unit 200 performs a body motion noise reduction process of reducing the body motion noise of the first detection signal detected by the first light receiving unit 141, based on the second detection signal detected by the second light receiving unit 142 and operates the biological information based on the first detection signal after performing the body motion noise reduction process.

By doing so, by providing a difference in at least one of the height in the position or the area corresponding to each light receiving unit and the distance between each light receiving unit and the light emitting unit, it is possible to mainly detect a pulse signal in the first light receiving unit 141 and to mainly detect body motion noise in the second light receiving unit 142. Accordingly, it is possible to perform the body motion noise reduction process using the second detection signal of the second light receiving unit 142, with respect to the first detection signal of the first light receiving unit 141 or to acquire biological information with high accuracy from the first detection signal after performing the body motion noise reduction process.

Figure 10:
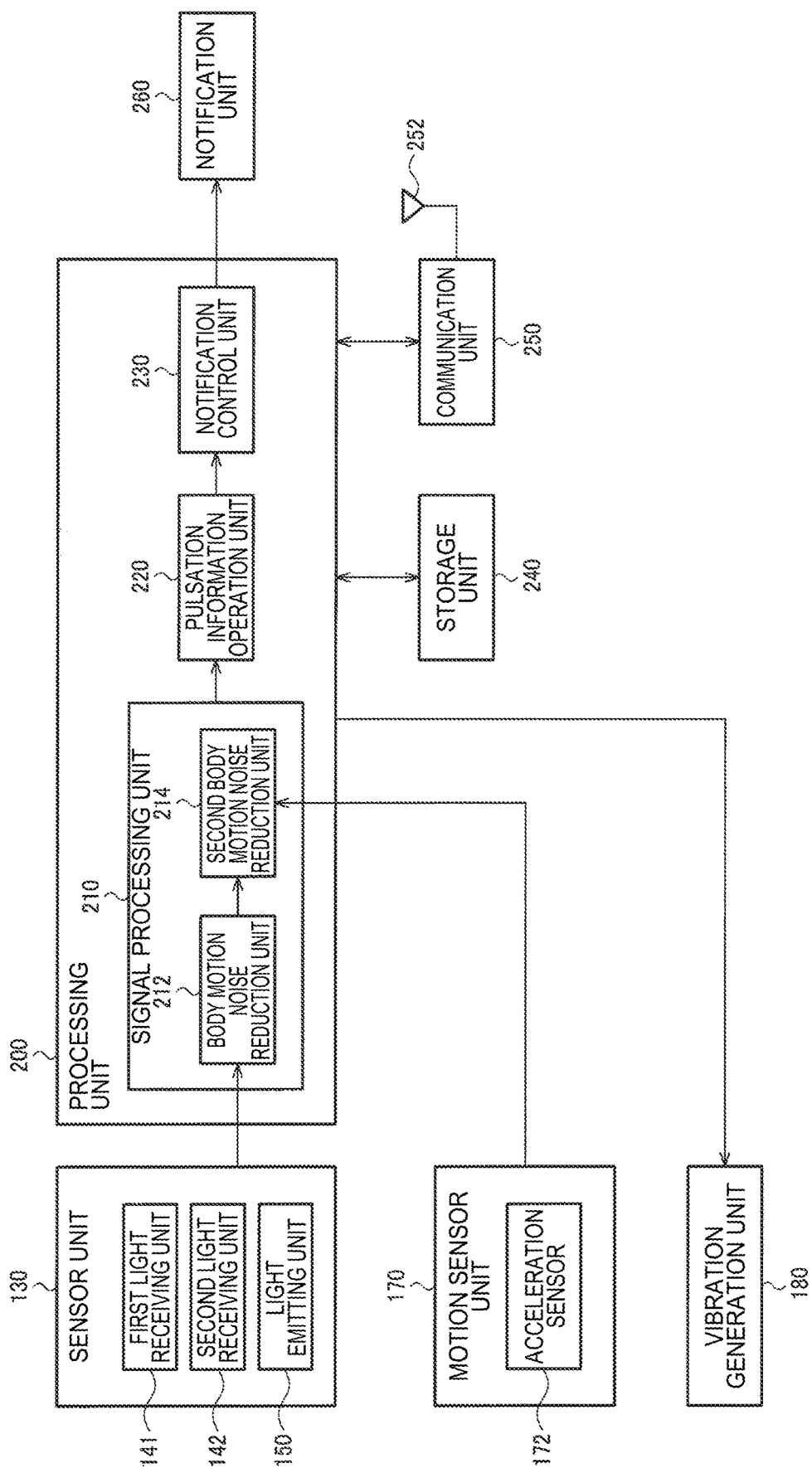
FIG. 10 is a functional block diagram of the biological information detection device.

FIG. 10 shows a functional block diagram of the biological information detection device of the embodiment. The biological information detection device in FIG. 10 includes the sensor unit 130, a motion sensor unit 170, a vibration generation unit 180, the processing unit 200, a storage unit 240, a communication unit 250, an antenna 252, and a notification unit 260. The biological information detection device of the embodiment is not limited to the configuration of FIG. 10, and various modifications can be performed by omitting a part of the constituent elements, replacing with other constituent elements, or adding other constituent elements.

The sensor unit 130 detects biological information such as a pulse wave and includes the first and second light receiving units 141 and 142 and the light emitting unit 150. Herein, the sensor unit 130 may include three or more light receiving units. An example where the light emitting unit 150 shares the plurality of light receiving units is shown as an example herein, but two or more light emitting units may be included without being limited to 1.

A pulse wave sensor (photoelectric sensor) is realized with the first and second light receiving units 141 and 142 and the light emitting unit 150. In a case of FIG. 10, a first pulse wave sensor is realized with the first light receiving unit 141 and the light emitting unit 150 and a second pulse wave sensor is realized with the second light receiving unit 142 and the light emitting unit 150. The sensor unit 130 outputs a signal detected by the plurality of pulse wave sensors as a detection signal (pulse wave detection signal).

The motion sensor unit 170 outputs a body motion detection signal which is a signal which changes depending on a body motion, based on sensor information of various motion sensors. The motion sensor unit 170 includes an acceleration sensor 172, for example, as a motion sensor. The motion sensor unit 170 may include a pressure sensor or a gyro sensor as the motion sensor.

The processing unit 200 performs various signal processes or control processes using the storage unit 240 as a working area, for example, and can be realized with a processor such as a CPU or a logic circuit such as ASIC, for example. The processing unit 200 includes a signal processing unit 210, a pulsation information operation unit 220, a notification control unit 230.

The signal processing unit 210 performs various signal processes (filter processes) and performs a signal process for a pulse wave detection signal from the sensor unit 130 or a body motion detection signal from the motion sensor unit 170.

For example, the signal processing unit 210 includes a body motion noise reduction unit 212 and a second body motion noise reduction unit 214. The body motion noise reduction unit 212 performs a body motion noise reduction process of reducing (removing) body motion noise which is noise due to a body motion from first detection signals of the first light receiving unit 141 based on the second detection signals of the second light receiving unit 142 among the pulse wave detection signals. The second body motion noise reduction unit 214 performs a second body motion noise reduction process of reducing body motion noise from first detection signals based on body motion detection signals from the motion sensor unit 170. Specifically, a spectrum subtraction method may be used in the body motion noise reduction process in the body motion noise reduction unit 212 and an adaptive filter or the like may be used in the second body motion noise reduction process in the second body motion noise reduction unit 214. The processes in the body motion noise reduction unit 212 and the second body motion noise reduction unit 214 will be described later in detail. In FIG. 10, the configuration of performing the second body motion noise reduction process in the second body motion noise reduction unit 214 after the body motion noise reduction process in the body motion noise reduction unit 212 is shown, but the order of the processes may be reversed and various modifications can be performed.

The pulsation information operation unit 220 performs an operation process of pulsation information based on the signals from the signal processing unit 210. The pulsation information is information such as a pulse rate, for example. Specifically, the pulsation information operation unit 220 performs a process of performing a frequency analysis process such as FFT for the pulsation detection signal after the noise reduction process by the body motion noise reduction unit 212 and the second body motion noise reduction unit 214 to acquire a spectrum and setting representative frequency in the acquired spectrum as a frequency of a pulse. A value which is 60 times of the acquired frequency is set as a pulse rate (heart rate) generally used. The pulsation information is not limited to the pulse rate and various other information items (for example, a frequency or a cycle of the pulse) representing a pulse rate may be used, for example. In addition, information regarding a pulsation state may be used or a value representing a blood volume may be used as pulsation information, for example.

The notification control unit 230 controls the notification unit 260. The notification unit 260 (notification device) notifies a user of various information items by the control of the notification control unit 230. As the notification unit 260, a light emitting unit for notification can be used, for example. In this case, the notification control unit 230 controls lighting on and off of the light emitting unit by controlling current flowing through the LED. The notification unit 260 may be a display unit such as an LCD or a buzzer.

The notification control unit 230 controls the vibration generation unit 180. The vibration generation unit 180 notifies a user of various information items by vibration. The vibration generation unit 180 can be realized by a vibration motor (vibrator), for example. The vibration motor generates vibration by rotating eccentric spindles, for example. Specifically, eccentric spindles are attached to both ends of a driving shaft (rotor shaft) to oscillate the motor. The vibration of the vibration generation unit 180 is controlled by the notification control unit 230. The vibration generation unit 180 is not limited to such a vibration motor and various modifications can be performed. For example, the vibration generation unit 180 can be realized by a piezoelectric element.

For example, notification of starting up when turning on the power source, notification of success of initial pulse wave detection, warning when a state where the pulse wave is not detected is continued for a certain period, notification at the time of movement of a fat burning zone, warning when battery voltage is decreased, notification of morning alarm, notification of a mail or a phone from a terminal device such as a smart phone, or the like can be performed by the vibration generated by the vibration generation unit 180. The information items may be notified by the light emitting unit for notification or may be notified by both of the vibration generation unit 180 and the light emitting unit.

The communication unit 250 performs a communication process such as near field communication, for example, with the external terminal device 420 as illustrated in FIG. 2. Specifically, the communication unit 250 performs a receiving process of a signal from the antenna 252 or a transmitting process of a signal to the antenna 252. The function of the communication unit 250 can be realized by a processer for communication or a logic circuit such as ASIC.

Figure 11:
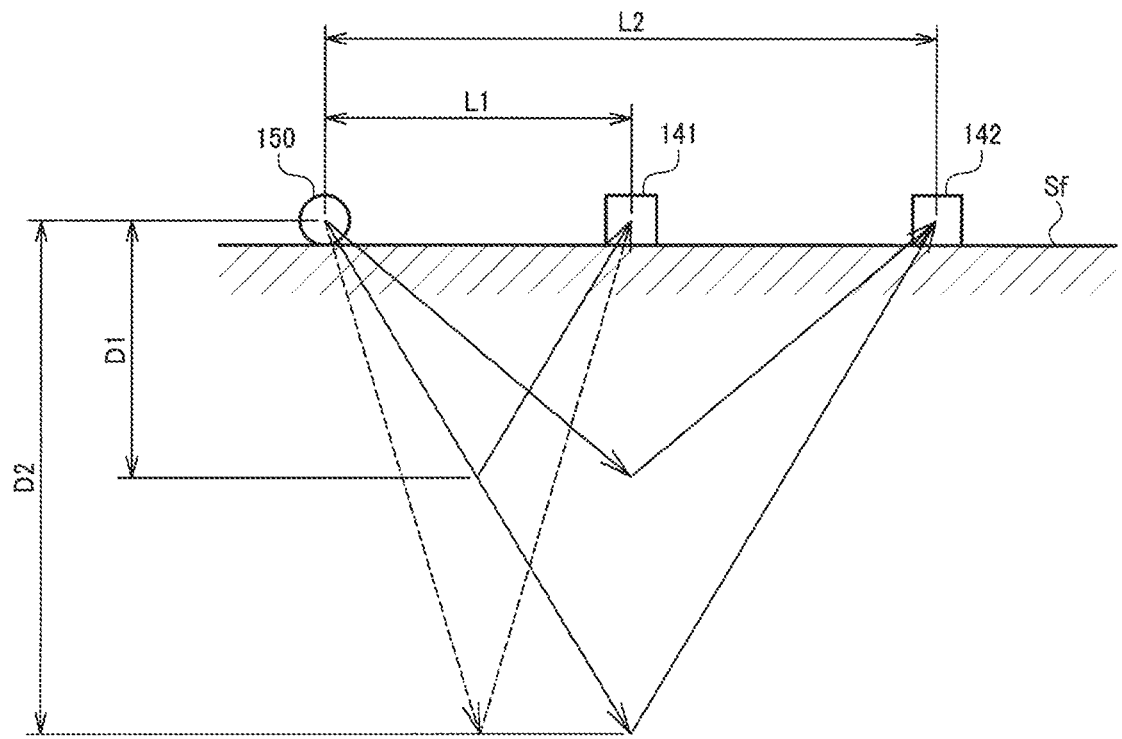
FIG. 11 is a diagram illustrating an effect of a distance between a light emitting unit and a light receiving unit affected on a penetration depth of light.

Next, the distance L1 between the light emitting unit 150 and the first light receiving unit 141 and the distance L2 between the light emitting unit 150 and the second light receiving unit 142 will be described. FIG. 11 is a diagram for illustrating effects of the distance between the light emitting unit and the light receiving unit affected on a penetration depth of light. The light emitting unit 150 and the first light receiving unit 141 and the light emitting unit 150 and the second light receiving unit 142 come into contact with a skin surface Sf of the wrist of a user. Herein, as described above, the light emitting unit 150 is shared by the two first and second light receiving units 141 and 142. In addition, in practice, the light transmitting member 30 comes into contact with the skin surface Sf as described above, the light transmitting member 30 may be omitted in order to simplify the description in FIG. 11.

It is found that, as the distance between the light emitting unit and the light receiving unit is short, sensitivity with respect to a deeper portion in the living body is decreased relatively compared to sensitivity with respect to a shallow portion. That is, the intensity of light which is emitted from the light emitting unit 150, reflected at a position of a depth D1 in a biological tissue, and returns to the first light receiving unit 141 is stronger than intensity of light which is reflected at a position of a depth D2 which is deeper than the depth D1 and returns to the first light receiving unit 141. Meanwhile, the intensity of light which is emitted from the light emitting unit 150, reflected at a position of the depth D1, and returns to the second light receiving unit 142 is stronger than intensity of light which is reflected at a position of a depth D2 and returns to the second light receiving unit 142, but the difference therebetween is not larger than that generated in the first light receiving unit 141. Accordingly, the first light receiving unit 141 is suitable for the measurement of the pulse wave in a blood vessel at a relatively shallower position than the case of the second light receiving unit 142.

Figure 12:
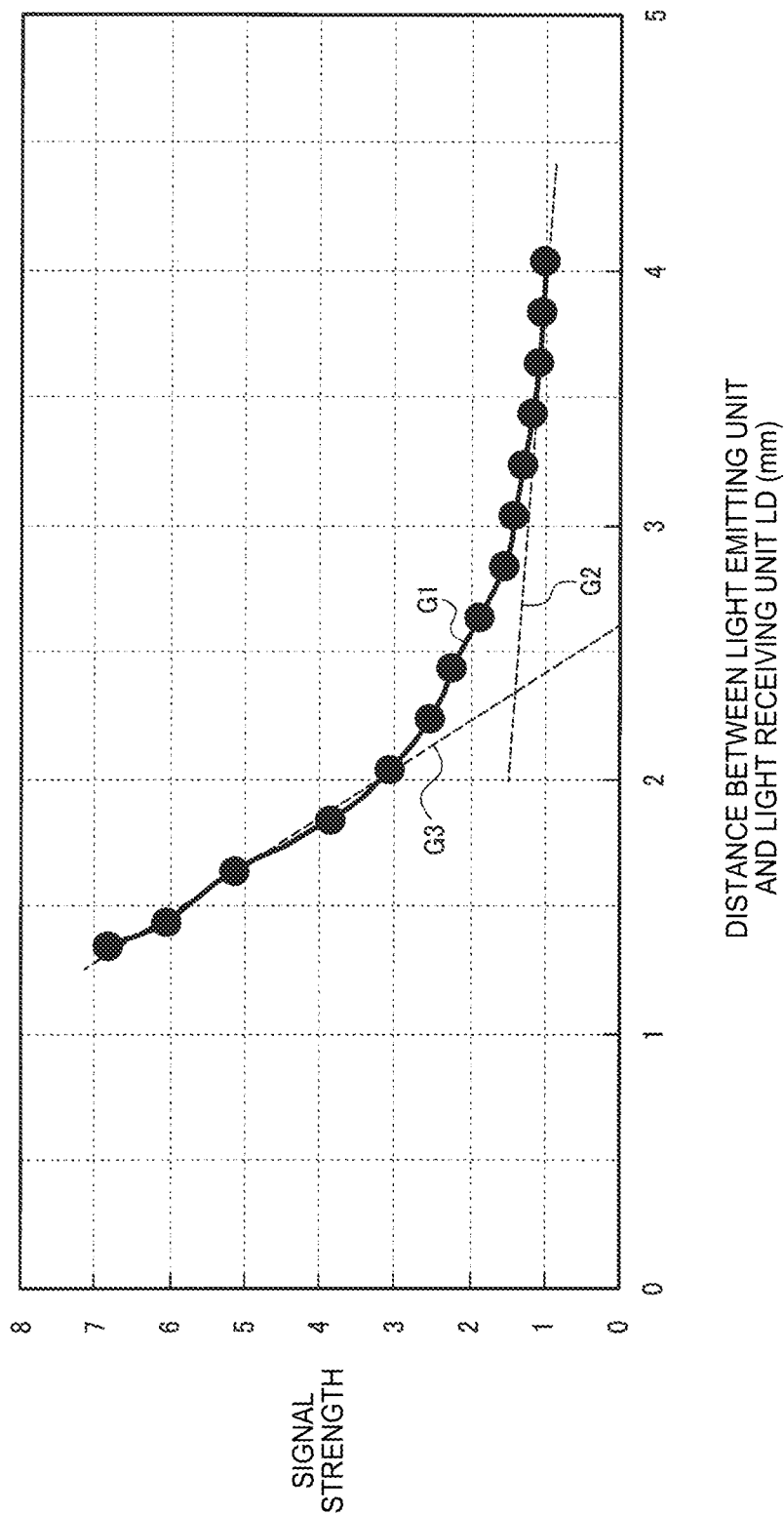
FIG. 12 is a diagram showing a relationship between the distance between the light emitting unit and the light receiving unit and signal strength of a detection signal.

FIG. 12 is a diagram showing a relationship between a distance LD between the light emitting unit 150 and the light receiving unit (141, 142) and signal strength. The distance LD between the light emitting unit 150 and the light receiving unit is a distance between center positions (representative positions) of the light emitting unit 150 and the light receiving unit, for example. For example, when the light receiving unit has a rectangular shape (approximately rectangular shape), the position of the light receiving unit is a center position of the rectangular shape. When the light emitting unit 150 includes the dome-type lens 152 as shown in FIG. 4, the position of the light emitting unit 150 is the center position (position of LED chip) of the lens 152, for example.

As shown from FIG. 12, as the distance LD between the light emitting unit 150 and the light receiving unit is short, the signal strength of the detection signal is increased and detection performance such as sensitivity is improved. Accordingly, the first light receiving unit 141 which mainly detects a pulse signal is desirably disposed to have the distance LD with the light emitting unit 150 as short as possible.

In this case, as shown in FIG. 12, the distance between the first light receiving unit 141 and the light emitting unit 150 desirably satisfies LD<3 mm. For example, as shown from a tangent G2 on the side of a long distance of a characteristic curve G1 of FIG. 12, the characteristic curve G1 is saturated in a range of LD≥3 mm. With respect to this, in a range of LD<3 mm, as the distance LD is decreased, the signal strength is increased. Accordingly, in this viewpoint, an expression of LD<3 mm is desired to be satisfied. The distance L1 between the light emitting unit 150 and the first light receiving unit 141 satisfies L1=1.0 mm to 3.0 mm.

Figure 13:
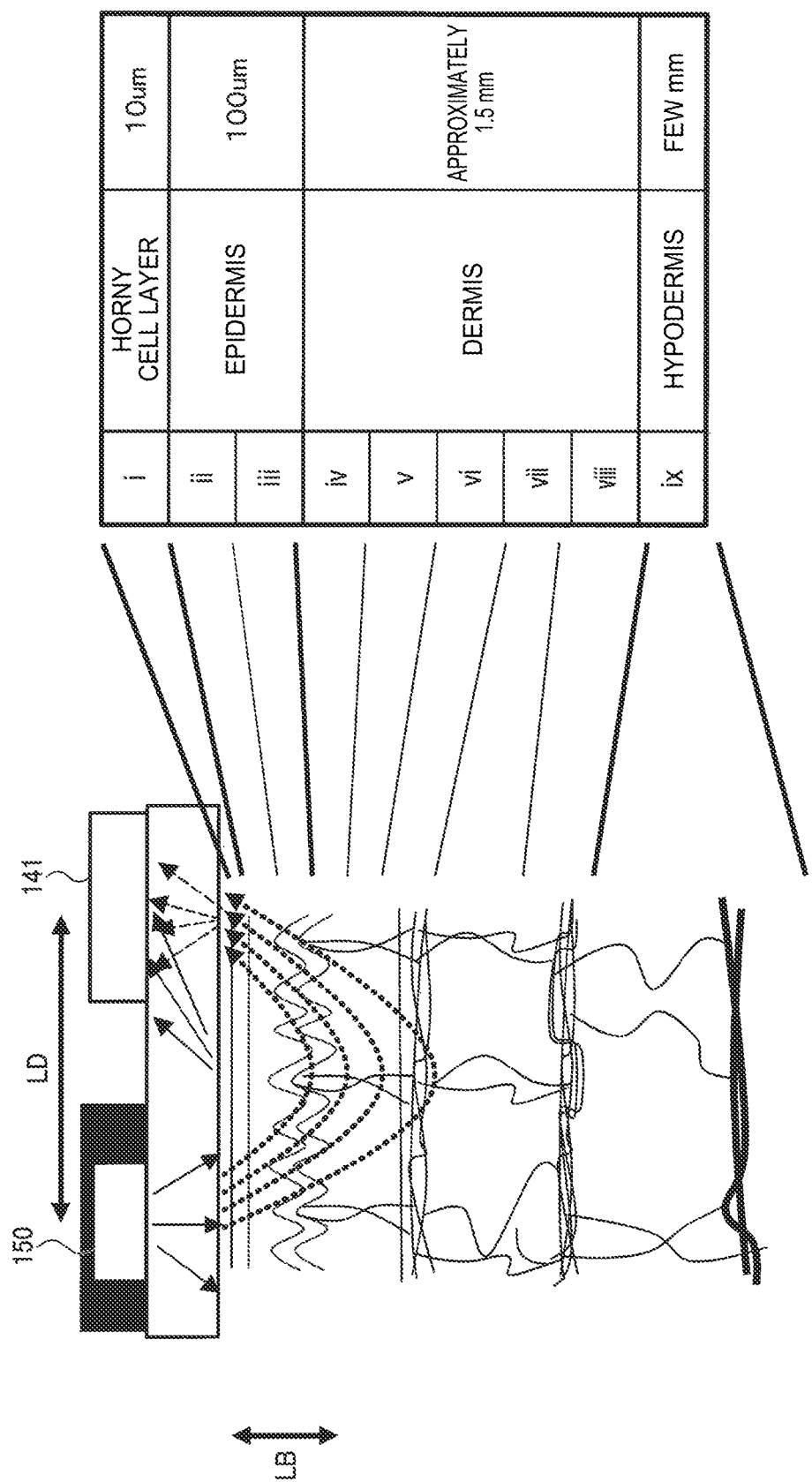
FIG. 13 is an explanatory diagram showing a relationship between the distance between the light emitting unit and the light receiving unit and a measurement distance in a depth direction.

There is a lower limit regarding the distance LD and it is not desirable to excessively decrease the distance LD. FIG. 13 is a schematic diagram showing that light emitted from the light emitting unit 150 is reflected and scattered in a living body and some of the light is received by the light receiving unit. In this case, the light from the light emitting unit 150 is diffused and scattered in a blood vessel of a subject, the light is incident to the light receiving unit, and a pulse wave is detected. In FIG. 13, a relationship of LD=2×LB is generally satisfied between the distance LD between the light emitting unit 150 and the light receiving unit and a measurement distance LB in a depth direction. For example, a measurement limitation distance by a light detection unit formed of the light emitting unit 150 and the light receiving unit which are separate from each other by the distance LD is LB=LD/2. There is no blood vessel which is a detection target of a pulse wave in a range where the distance LB is, for example, from 100 µm to 150 µm. Accordingly, when the distance LD satisfies an expression of LD 2×LB=2×100 µm to 2×150 µm)=0.2 mm to 0.3 mm, it is assumed that the detection signal of the pulse wave is extremely small. That is, when the distance LD is short, the measurement distance LB in the depth direction is also decreased, and when the detection target is not present in the range of the distance LB, the detection signal is extremely decreased. That is, the detection performance is improved as the distance LD is short, but there is limitation and a lower limit exists. In the embodiment, it is necessary to detect the pulse signal at sufficient strength in the first light receiving unit 141, and accordingly an expression of L1≥1.0 mm is set. That is, an expression of 1.0≤mm L1≤3.0 mm is desirable.

With respect to this, the distance L2 between the light emitting unit 150 and the second light receiving unit 142 may be set so that the sensitivity with respect to the pulse signal is low and the sensitivity with respect to the body motion noise is high, compared to the first light receiving unit 141. For example, when an expression of L2>3.0 mm (or L2<1.0 mm) is satisfied, a degree of the pulse signal is decreased and a degree of the body motion noise is increased (MN ratio is decreased), compared to a case of the first light receiving unit 141 satisfying an expression of 1.0 mm≤L1≤3.0 mm.

However, in the second light receiving unit 142, the MN ratio (M represents a pulse signal, N represents noise, and a MN ratio is a ratio between the pulse signal and noise (generally SN ratio)) of the detection signal may be sufficiently decreased compared to the MN ratio of the detection signal of the first light receiving unit 141. That is, instead of a point of setting the distance to have an absolute value as L2>3.0 mm (or L2<1.0 mm), a point of changing the value of L2 with respect to L1 may be considered, so as to have a difference between the first and second detection signals to some extent (for example, a degree so as to perform the noise reduction process by a spectrum subtraction method will be described later).

Herein, a relationship of L1 and L2 for causing a difference in the first and second detection signals may be, for example, L2>2×L1. In this case, when L1=2.0 mm, L2>4.0 mm, and accordingly, a relationship of L2=5.6 mm may be satisfied, and the pulse signal is detected at certain strength, but conditions of the small MN ratio of the second detection signal compared to the first detection signal setting shorter L1 can be satisfied. The distance LD between the light emitting unit 150 and the light receiving unit may be a distance from the center of the light emitting unit 150 to the center of the light receiving unit in a sectional view or a plan view, or may be a distance from the end portion of the light emitting unit 150 on the light receiving unit side to the end portion of the light receiving unit on the light emitting unit 150 side.

It is known that the sensitivity with respect to the pulse signal or body motion noise also changes depending on the pressing force against a subject.

Figure 14:
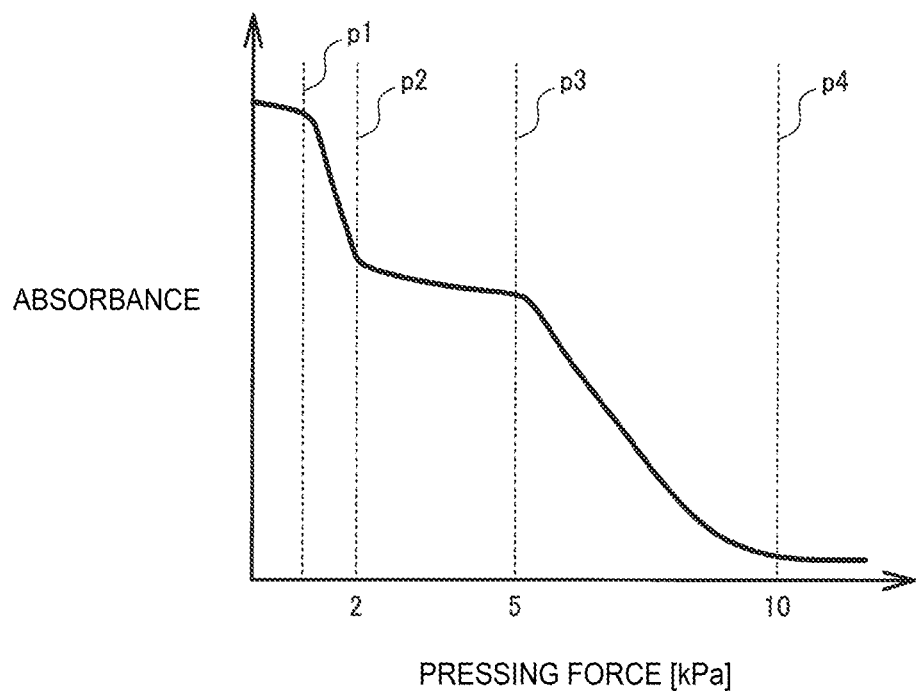
FIG. 14 is a diagram illustrating a change in absorbance with respect to a pressing force.

FIG. 14 is a diagram illustrating a change in absorbance with respect to a pressing force. A horizontal axis indicates a pressing force and a vertical axis indicates absorbance. When the pressing force changes, the affected blood vessel changes. A blood vessel which is most easily affected, that is, a blood vessel which is affected with a lowest pressing force is a capillary. In the example of FIG. 14, an amount of change in absorbance is great when the pressing force exceeds p1, and this means that the capillary is started bursting due to the pressing force. When the pressing force exceeds p2, the change in absorbance becomes slow, and this means that the capillary is substantially completely burst (closed). An artery is affected next to the capillary. When the pressing force is further increased to exceed p3, the amount of change in absorbance becomes great again, and this means that the artery is started bursting. When the pressing force exceeds p4, the change in absorbance becomes slow, and this means that the artery is substantially completely burst (closed).

In the embodiment, the second light receiving unit 142 increases the ratio of the body motion noise by detecting a signal corresponding to the capillary and the first light receiving unit 141 increases the ratio of the pulse signal by measuring a signal (pulse signal) corresponding to the artery. Accordingly, the pressing force of the second light receiving unit 142 is designed to be in the range from p1 to p2 and the pressing force of the first light receiving unit 141 is designed to be in the range from p3 to p4. A difference in the pressing force between the first light receiving unit 141 and the second light receiving unit 142 is desirably from 2.0 kPa to 8.0 kPa, for example.

Figure 15:
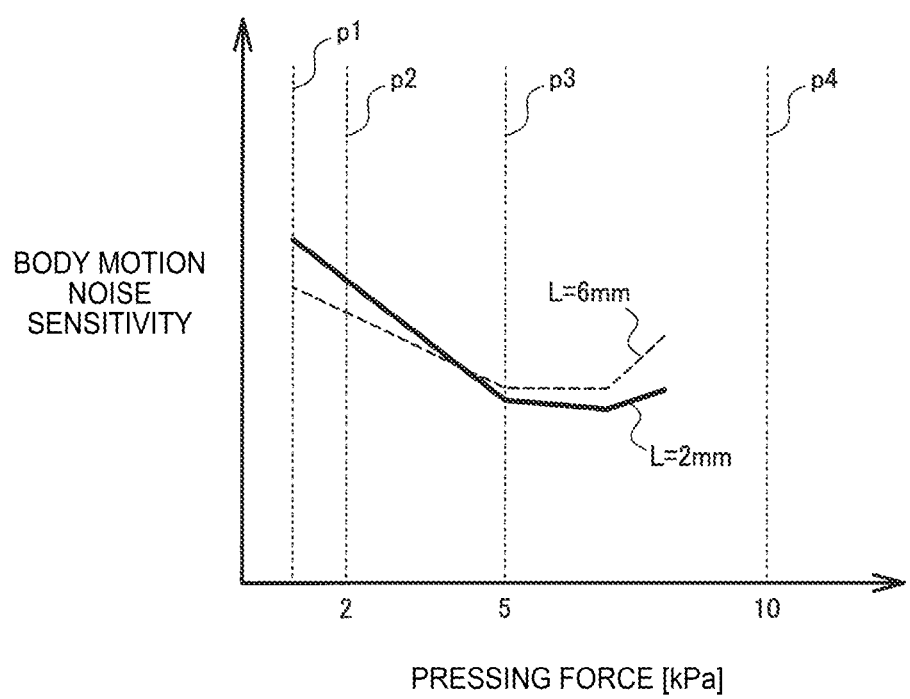
FIG. 15 is a diagram illustrating a change in body motion noise sensitivity with respect to a pressing force.

FIG. 15 is a diagram illustrating a change in body motion noise sensitivity with respect to the pressing force. In FIG. 15, an example where the distance L from the light emitting unit to the light receiving unit is 2 mm and an example where the distance L is 6 mm are shown together. In both examples where the distance L is 2 mm and 6 mm, as the pressing force is low, the noise sensitivity tends to be high, and as the pressing force is high, the noise sensitivity tends to be low. This is considered that, since blood flowing the capillary easily moves by the body motion, noise due to the body motion is easily included in the light reflected by the capillary which exists in a comparatively shallow position in the biological tissue.

Figure 16:
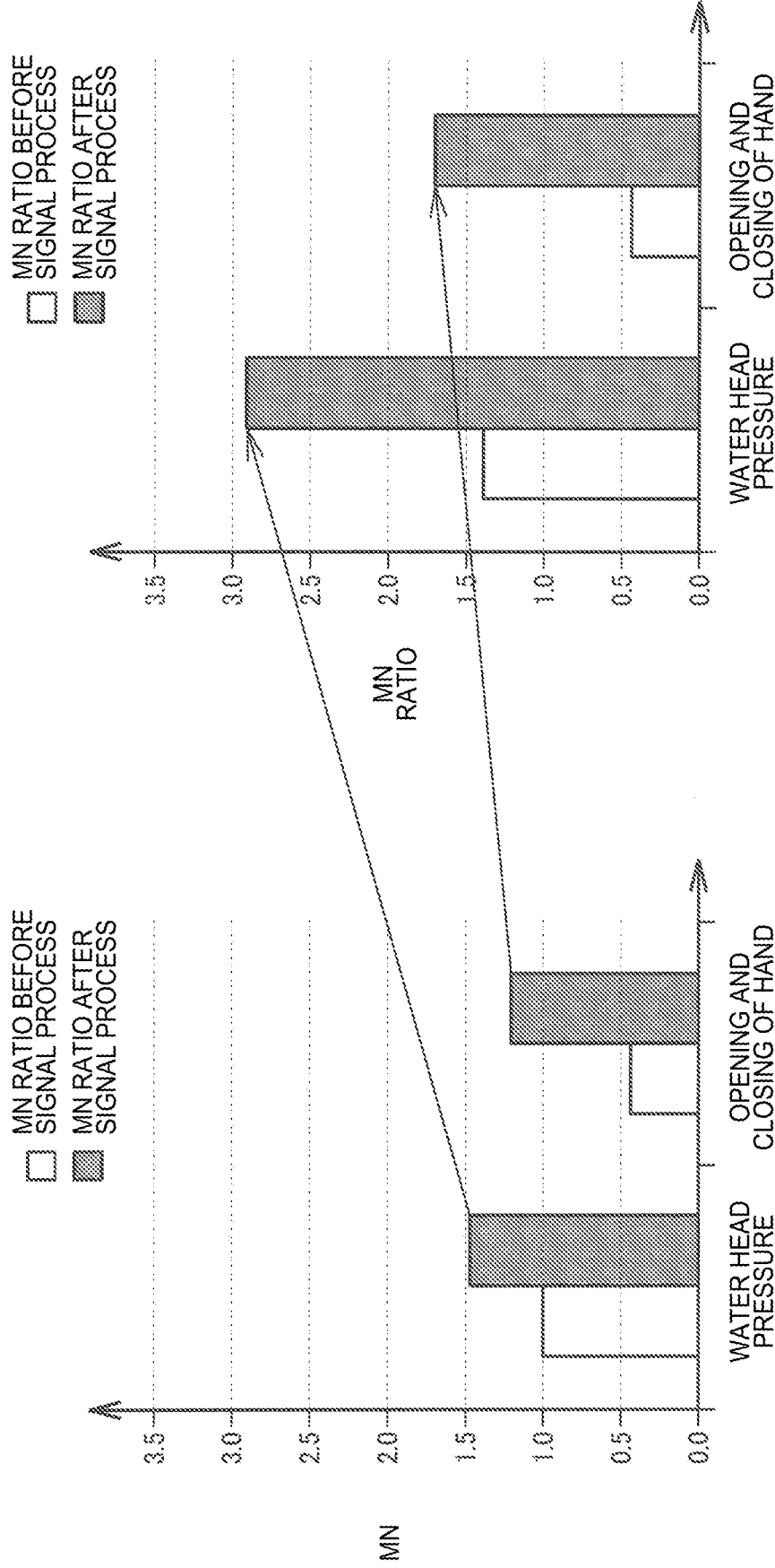
FIGS. 16A and 16B are diagrams illustrating a degree of improvement of a MN ratio (SN ratio) obtained by a noise reduction process, when a difference between a pressing force is provided and is not provided.

FIG. 16A shows a change in the MN ratio of the first detection signal before and after the body motion noise reduction process, when a difference in the pressing force is not provided between the first light receiving unit 141 and the second light receiving unit 142 and the difference is only provided for the distances L1 and L2 with the light emitting unit 150. Herein, changing of water head pressure and an operation of opening and closing the hand are performed as motions of a user which cause generation of the body motion noise, and a degree of reduction of the body motion noise corresponding to each operation is measured. The motion of changing the water head pressure is a motion of changing the height of the measurement position with respect to the heart and, specifically, can be realized by an operation of lifting arm up and down. The opening and closing of the hand can be realized by an operation of mutually performing a state of clenching a first by bending all fingers and a state of opening the hand by stretching fingers. As shown in FIG. 16A, it is possible to check the reduction effects of the body motion noise, by only providing the difference in distances.

With respect to this, FIG. 16B shows a change in the MN ratio of the first detection signal before and after the body motion noise reduction process, when the difference between the distances L1 and L2 with the light emitting unit 150 is provided and the difference in the pressing force between the first light receiving unit 141 and the second light receiving unit 142 is also provided. As shown in comparison with FIG. 16A and FIG. 16B, it is found that the reduction effects of the body motion noise are improved by also providing the difference in the pressing force. Accordingly, herein, a case of providing both the difference in distances and the difference in the pressing force will be described.

That is, when measuring the biological information of a subject, when the pressing force in the position or the area of the light transmitting member 30 corresponding to the first light receiving unit 141 is set as P1 and the pressing force in the position or the area of the light transmitting member 30 corresponding to the second light receiving unit 142 is set as P2, a relationship of P1>P2 is satisfied. By doing so, as described above, the first detection signal from the first light receiving unit 141 and the second detection signal from the second light receiving unit 142 can have a difference in characteristics.

Specifically, the difference in the pressing force may be realized by a difference in heights of the light transmitting member 30 coming into contact with a subject. As described above, the pressing force is set to be high in the first light receiving unit 141 which mainly detects the pulse signal and the pressing force is set to be low in the second light receiving unit 142 compared to the first light receiving unit 141. Accordingly, as shown in FIG. 9A, a height h1 of the light transmitting member in the position or the area corresponding to the first light receiving unit 141 may be greater than a height h2 of the light transmitting member in the position or the area corresponding to the second light receiving unit 142.

Figure 17:
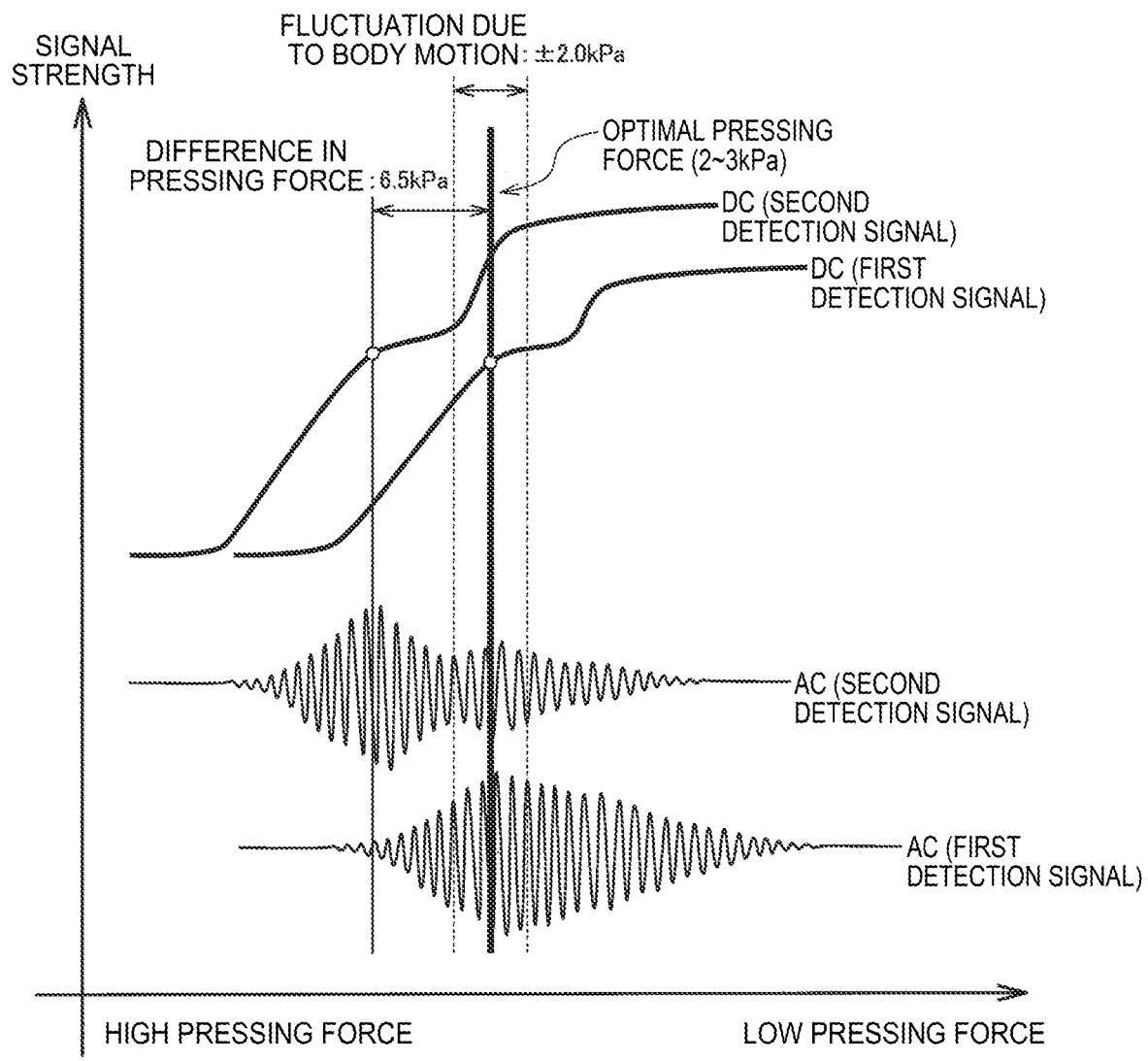
FIG. 17 is a relationship diagram of a pressing force and a DC component and an AC component detected by each light receiving unit.

This is because that, as the height is great, the component is exposed to a subject side, and accordingly, when the biological information detection device is fixed to the wrist with a predetermined pressing force, the pressing force corresponding to the first light receiving unit 141 with great height of the light transmitting member 30 can be higher than the pressing force corresponding to the second light receiving unit 142 with small height of the light transmitting member 30. FIG. 17 shows this as an example.

A horizontal axis of FIG. 17 represents a pressing force (pressing force by load mechanism configured with the bands 320 and 322 or the expansion and contraction portions 330 and 332 of FIG. 1) and a vertical axis represents DC and AC components of the detection signal. As shown with the DC signal shown on the upper portion of FIG. 17, in the first light receiving unit 141 where the pressing force is comparatively high, the pressing force to some extent is added even in a state where the pressing force is comparatively low, and the DC component is prevented. With respect to this, since the pressing force is comparatively low in the second light receiving unit 142, a prevention degree of the DC components is smaller than that in the first detection signal, in a given pressing force state. Accordingly, in a range of the "optimal pressing force" shown in FIG. 17, since the pressing force corresponding to the first light receiving unit 141 is in a range from p3 to p4 (FIGS. 14 and 15), the noise is prevented and the signal level of the pulse signal is increased. Meanwhile, since the pressing force of the second light receiving unit 142 is in the range of p1 to p2 (FIGS. 14 and 15), the noise is insufficiently prevented and the ratio of the body motion noise is increased.

This is also clear from the comparison with the AC component shown on the lower portion of FIG. 17, and the first detection signal has a high level signal of the AC component and the second detection signal has a low level signal of the AC component in the range of the optimal pressing force. Since the pulse signal is shown in the change of the detection signal, that is, the AC component as described above, FIG. 17 shows that the ratio of the body motion noise of the second light receiving unit 142 is relatively high, whereas the first light receiving unit 141 can sufficiently detect the pulse signal.

Hereinafter, the difference in height of the light transmitting member 30 will be described with reference to the drawings in detail. As shown in FIGS. 9A and 9B described above, the first protrusion 31 is provided for a first photoelectric sensor realized by the light emitting unit 150 and the first light receiving unit 141 and the second protrusion 32 is provided for a second photoelectric sensor realized by the light emitting unit 150 and the second light receiving unit 142.

At that time, when a direction (DR3) from the biological information detection device to a subject is a height direction in a state where the biological information detection device is mounted, the height h1 of the light transmitting member 30 in a position or an area corresponding to the first light receiving unit 141 is greater than the height h2 of the light transmitting member 30 in a position or an area corresponding to the second light receiving unit 142. Various modifications can be performed for defining the height, and the distance from a surface where the light emitting unit 150 or the like is formed among the area of the substrate 160 shown in FIG. 9A may be set as a height. Alternatively, the thickness of the light transmitting member 30 may be set as a height.

Alternatively, in the biological information detection device, a reference surface is set to be provided on the side (lower side of FIG. 9A) opposite to a subject with respect to the substrate 160 and parallel to the substrate 160 and the distance from the reference surface may be set as a height of the light transmitting member 30. This reference surface may be any member (for example, main substrate where the processing unit 200 is mounted) or may be a virtual surface.

Definitions of the position or area corresponding to each light receiving unit are also considered in various ways. For example, the height h1 is a height of the light transmitting member 30 in the representative position of the first light receiving unit 141 and the height h2 is a height of the light transmitting member 30 in the representative position of the second light receiving unit 142. For the representative position herein, the center position of each light receiving unit may be used, for example.

In this case, the center position of the first light receiving unit 141 is A1 of FIG. 9B and the center position of the second light receiving unit 142 is A2. As shown in FIG. 9A, the height of the light transmitting member 30 in the center position A1 of the first light receiving unit 141 defines an intersection between a linear line extended from A1 in the DR3 direction and the surface of the light transmitting member 30 (surface coming into contact with a subject when mounting), and the height h1 of the light transmitting member 30 of the intersection may be used. In the same manner as described above, the height of the light transmitting member 30 in the center position A2 of the second light receiving unit 142 is set as h2 of FIG. 9A.

Alternatively, when the area including the first light receiving unit 141 and the light emitting unit 150 in a plan view seen from the subject side is set as a first area and the area including the second light receiving unit 142 and the light emitting unit 150 is set as a second area, the height h1 may be an average height of the light transmitting member 30 in the first area and the height h2 may be an average height of the light transmitting member 30 in the second area. Various areas can be assumed as the areas including the light emitting unit and the light receiving unit, and a minimum rectangular area including the light emitting unit and the light receiving unit may be considered as an example.

The height of the light transmitting member in the area corresponding to the first light receiving unit 141 defines an intersection between the linear line extended from each point included in the first area in the DR3 direction and the surface of the light transmitting member 30, and the heights of the light transmitting member 30 in the intersection may be averaged for obtaining the height.

In FIG. 9A, the pressing force prevention unit 60 is provided. The pressing force prevention unit 60 is, for example, provided so as to surround the first and second protrusions 31 and 32 of the light transmitting member 30 and, for example, prevents the pressing force applied to a subject by the first protrusion 31 or the like.

In this case, when the height of the first protrusion 31 in the direction DR3 from the biological information detection device to a subject is set as h1, a height of the pressing force prevention unit 60 is set as h3, and a value obtained by subtracting the height h3 from the height h1 (difference between the heights h1 and h3) is set as $\Delta h$, a relationship of $\Delta h = h1 - h3 > 0$ is satisfied. For example, the first protrusion 31 is protruded on the subject side from the pressing force prevention surface of the pressing force prevention unit 60 so as to satisfy a relationship of $\Delta h > 0$. That is, the first protrusion 31 is protruded to the subject side more than the pressing force prevention surface of the pressing force prevention unit 60 by the amount of $\Delta h$.

As described above, by providing the first protrusion 31 so as to satisfy a relationship of $\Delta h > 0$, it is possible to apply an initial pressing force for exceeding a vein vanishing point to a subject. By providing the pressing force prevention unit 60 for preventing the pressing force applied to a subject by the first protrusion 31, the pressing force fluctuation can be prevented to be minimum in a usage range for performing the measurement of the biological information by the biological information detection device and the reduction of the noise component or the like is realized. The vein vanishing point herein is a point where a signal caused by the vein superimposed in the pulse wave signal is vanished or becomes small so as not to affect the pulse wave measurement, when the first protrusion 31 comes into contact with a subject and the pressing force is gradually increased.

Specifically, the pressing force prevention unit 60 prevents the pressing force applied to a subject by the first protrusion 31, so that a pressing force change amount VF2 in a second load range RF2 where a load of the load mechanism is larger than FL1 becomes small, compared to a pressing force change amount VF1 in a first load range RF1 where a load of the load mechanism (bands and expansion and contraction portions) of the biological information detection device is 0 to FL1. That is, the pressing force change amount VF1 increases in the first load range RF1 which is the initial pressing force range, while the pressing force change amount VF2 decreases in the second load range RF2 which is the usage range of the biological information detection device.

That is, in the first load range RF1, the pressing force change amount VF1 increases and inclination of change characteristics of the pressing force with respect to the load also increases. The pressing force with large inclination of the change characteristics is realized with Δh corresponding to the protruded amount of the first protrusion 31. That is, by providing the first protrusion 31 so as to satisfy a relationship of Δh>0, even when the load by the load mechanism is small, it is possible to apply the sufficient initial pressing force necessary for exceeding the vein vanishing point to a subject.

Meanwhile, in the second load range RF2, the pressing force change amount VF2 decreases and inclination of change characteristics of the pressing force with respect to the load also decreases. The pressing force with small inclination of the change characteristics is realized by pressing force prevention performed by the pressing force prevention unit 60. That is, since the pressing force prevention unit 60 prevents the pressing force applied to a subject by the first protrusion 31, even when the fluctuation in load occurs in the usage range of the biological information detection device, the fluctuation in pressing force can be prevented to be minimum. Accordingly, the noise components are reduced.

Finally, the body motion noise reduction process performed by the processing unit 200 of FIG. 10 will be described. Specifically, the spectrum subtraction method performed based on the second detections signal and the adaptive filter process performed based on the signal from the motion sensor will be described.

Figure 18A:
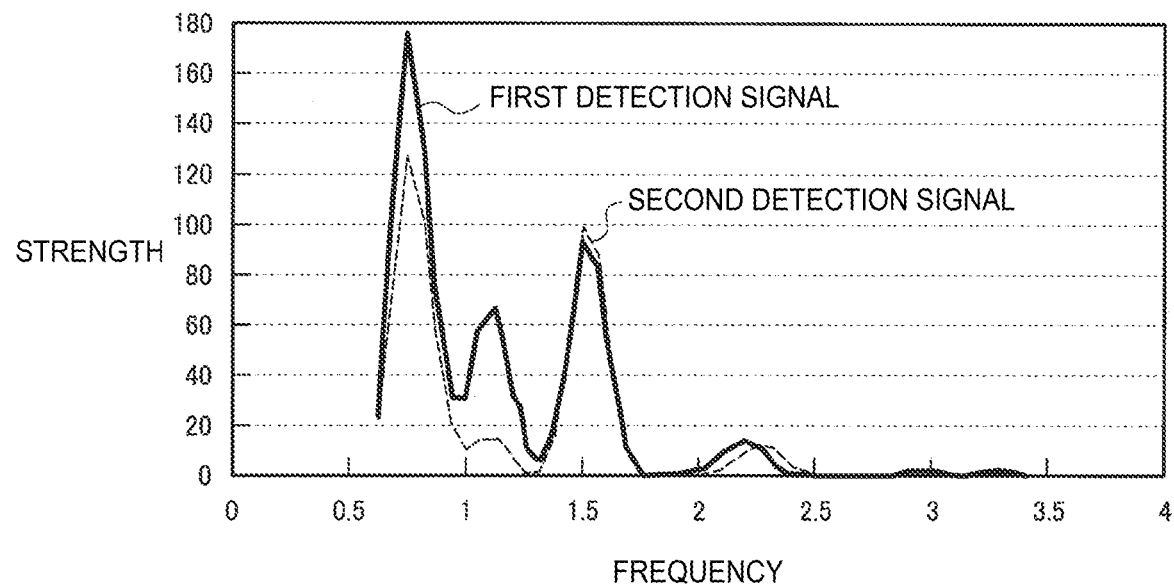
FIGS. 18A and 18B are explanatory diagrams of a body motion noise reduction process using a second detection signal.
Figure 18B:
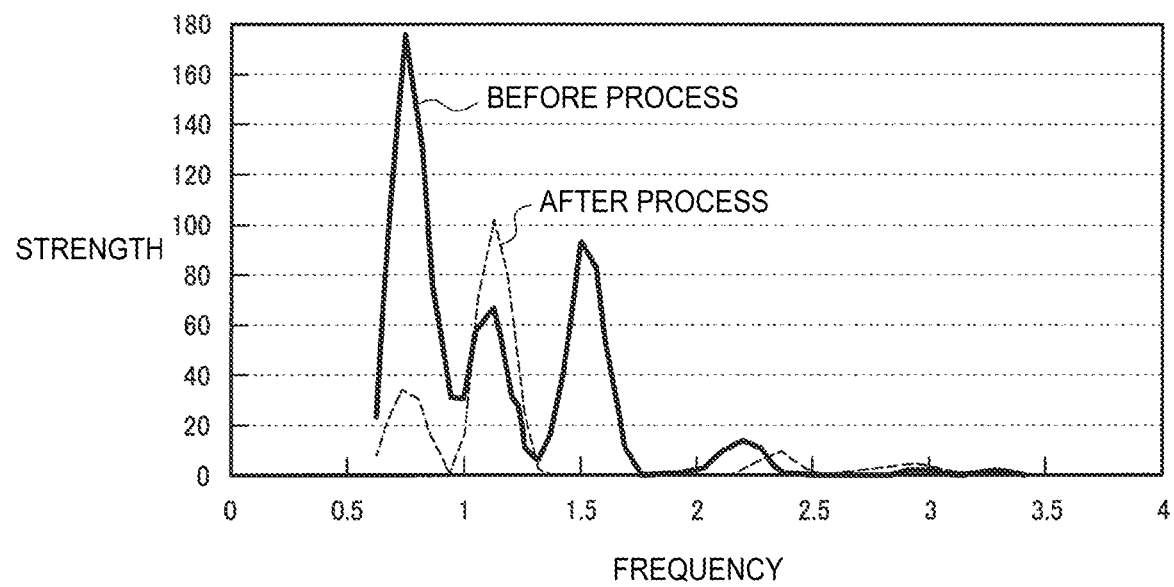

FIGS. 18A and 18B are diagrams illustrating the noise reduction process of the first detection signal based on the second detection signal using the spectrum subtraction method. In the spectrum subtraction method, the spectrum is obtained by performing frequency conversion process for the first and second detection signals. The noise spectrum is assumed from the spectra of the second detection signal and a process of removing the assumed noise spectrum from the spectra of the first detection signal is performed.

FIG. 18A shows the spectrum of the first detection signal and the spectrum of the second detection signal actually acquired. As described above, by using the biological information detection device according to the embodiment, the spectrum of the second detection signal is mainly the spectrum corresponding to the noise component. That is, it can be assumed that the frequency with a high peak in the spectrum of the second detection signal is a frequency corresponding to the body motion noise. In practice, only peak may be subtracted among the spectra of the second detection signal, but the embodiment is not limited thereto, and a process of subtracting the entire spectra of the second detection signal from the entire spectra of the first detection signal may be performed, for example.

When performing the subtraction, a coefficient of one of the first detection signal and the second detection signal is multiplied, for example, so as to set off the noise. This coefficient is acquired from the signal strength of the predetermined frequency, for example. Alternatively, the noise and signal are separated by a method such as clustering, for example, and a coefficient is calculated by setting the noise of the first detection signal and the noise of the second detection signal to have the same strength.

FIG. 18B shows an example of the first detection signal before and after the body motion noise reduction process by the spectrum subtraction method. As shown in FIG. 18B, the body motion noise shown at 0.7 Hz to 0.8 Hz (pulse rate of 42 to 48) and 1.5 Hz (pulse rate of 90) is prevented to be small by the body motion noise reduction process, and a possibility of erroneous determination that these are the pulse signal can be prevented. Meanwhile, the spectrum corresponding to the pulse signal shown approximately at 1.1 Hz (pulse rate of 66) can maintain the signal level without being reduced.

Since the spectrum subtraction method is realized by a frequency conversion process such as fast fourier transform (FFT) and a subtraction process of the spectrum, it is advantageous that an algorithm is simple and the calculation amount is small. In addition, since there is no learning elements as in the adaptive filter process will be described later, instant responsiveness is high.

The embodiments have been described in detail hereinabove, but a person skilled in the art can easily ascertain that various modifications can be performed in a range of substantially not departing from the new matters and effects of the invention. Accordingly, all modification examples are included in the scope of the invention. For example, in the specification or the drawings, the terms used in the broader sense or used with other terms having the same meaning at least once can be replaced with the other terms in any portions of the specification or the drawings. The configuration and operation of the biological information detection device are not limited to the embodiments and various modifications can be performed.

What is claimed is:

1. A sensor comprising:
   a light emitting unit which irradiates a subject with light;
   a first light receiving unit which receives the light from the subject;
   a second light receiving unit which receives the light from the subject; and
   a beam which is provided between the first light receiving unit and the second light receiving unit, in a plan view in a vertical direction of a light receiving surface of the first light receiving unit,
   wherein
   the first light receiving unit and the second light receiving unit are disposed along a first direction, and
   when a first distance in the first direction between a first end portion of the beam on a first light receiving unit side and a second end portion of the first light receiving unit on a second light receiving unit side is set as LE1, and a second distance in the first direction between a third end portion of the beam on the second light receiving unit side and a fourth end portion of the second light receiving unit on the first light receiving unit side is set as LE2, a relationship of LE1>LE2 is satisfied.

2. The sensor according to claim 1, further comprising:
   a light transmitting member which is provided on a first position on a subject side with respect to the first light receiving unit and the second light receiving unit, passes the light from the subject, and comes into contact with the subject when measuring biological information of the subject to apply a pressing force.

3. The sensor according to claim 2,
   wherein the light transmitting member includes a first protrusion corresponding to the first light receiving unit and a second protrusion corresponding to the second light receiving unit, and the beam shields light so that light which has passed a boundary between the first protrusion and the second protrusion is not incident to the light receiving surface of the first light receiving unit.

4. The sensor according to claim 2,
wherein the light transmitting member includes a first protrusion corresponding to the first light receiving unit and a second protrusion corresponding to the second light receiving unit, and
the beam is positioned on a second position so as not to shield the light which
passes a third position on a second protrusion side other than a total reflection boundary of the first protrusion and
is incident to a point where a third distance to the beam is shortest among the light receiving surface of the second light receiving unit.

5. The sensor according to claim 2,
wherein the light transmitting member includes a first protrusion corresponding to the first light receiving unit and a second protrusion corresponding to the second light receiving unit, and
the sensor further includes a pressing force prevention unit which is provided so as to cover the first and second protrusions and prevents a pressing force applied to the subject by the first protrusion.

6. The sensor according to claim 2,
wherein, when a first height of the light transmitting member in a second position or a first area corresponding to the first light receiving unit in a direction from a biological information detection device to the subject is set as h1 and a second height of the light transmitting member in a third position or a second area corresponding to the second light receiving unit is set as h2, an additional relationship of h1>h2 is satisfied.

7. The sensor according to claim 1,
wherein the first light receiving unit is disposed between the light emitting unit and the second light receiving unit.

8. The sensor according to claim 1, further comprising:
a processing unit which processes biological information of the subject based on a first detection signal detected by the first light receiving unit.

9. The sensor according to claim 8,
wherein the processing unit performs a noise reduction process of the first detection signal based on a second detection signal detected by the second light receiving unit.

10. The sensor according to claim 1, further comprising:
a light shielding member which is provided so as to surround at least the first light receiving unit and the second light receiving unit, and includes a first opening corresponding to the first light receiving unit and a second opening corresponding to the second light receiving unit,
wherein the beam is provided between the first opening and the second opening.

11. The sensor according to claim 1, further comprising:
a light shielding member which includes first to third light shielding surfaces and the beam,
wherein the first light shielding surface is provided between the light emitting unit and the first light receiving unit, and
the second light shielding surface and the third light shielding surface are provided so as to intersect the first light shielding surface.

12. The sensor according to claim 11, wherein the light shielding member is formed by sheet metal working of metal.

13. The sensor according to claim 11,
wherein the first light shielding surface and the second light shielding surface are provided so as to be adjacent to each other through a first gap area, and the first light shielding surface and the third light shielding surface are provided so as to be adjacent to each other through a second gap area.

14. The sensor according to claim 11,
wherein a first opening corresponding to the first light receiving unit is provided by the first light shielding surface, the second light shielding surface, the third light shielding surface, and the beam.

15. The sensor according to claim 11,
wherein a first opening corresponding to the first light receiving unit is provided by the first light shielding surface, the beam, and eaves.

16. The sensor according to claim 10,
wherein the light shielding member includes a protrusion, and
the protrusion is provided so that an attachment surface of the protrusion is positioned at a distance of a height HB (HB>0) from an installation surface of the substrate to which the light shielding member is mounted.

17. A biological information detection device on which the sensor according to claim 1 is mounted.

18. A biological information detection device on which the sensor according to claim 2 is mounted.

19. A sensor comprising:
a light emitting unit which irradiates a subject with light;
a first light receiving unit which receives the light from the subject;
a second light receiving unit which receives the light from the subject;
a beam which is provided between the first light receiving unit and the second light receiving unit, in a plan view in a vertical direction of a light receiving surface of the first light receiving unit; and
a light transmitting member which is provided on a first position on a subject side with respect to the first light receiving unit and the second light receiving unit, passes the light from the subject, and comes into contact with the subject when measuring biological information of the subject to apply a pressing force,
wherein
the light transmitting member includes a first protrusion corresponding to the first light receiving unit and a second protrusion corresponding to the second light receiving unit, and
the beam is positioned on a second position so as not to shield the light which
passes a third position on a second protrusion side other than a total reflection boundary of the first protrusion and
is incident to a point where a distance to the beam is shortest among the light receiving surface of the second light receiving unit.

20. A sensor comprising:
a light emitting unit which irradiates a subject with light;
a first light receiving unit which receives the light from the subject;
a second light receiving unit which receives the light from the subject;
a beam which is provided between the first light receiving unit and the second light receiving unit, in a plan view in a vertical direction of a light receiving surface of the first light receiving unit; and a light transmitting member which is provided on a position on a subject side with respect to the first light receiving unit and the second light receiving unit and which includes a first protrusion corresponding to the first light receiving unit and a second protrusion corresponding to the second light receiving unit, wherein the first protrusion has a first radius of curvature, the second protrusion has a second radius of curvature, the second radius of curvature different than the first radius of curvature, and the first protrusion overlaps the second protrusion when viewed in the plan view.

* * * * *